United States Patent [19]

Takeda

[11] Patent Number: 5,626,141
[45] Date of Patent: *May 6, 1997

[54] BLOOD PRESSURE MEASUREMENT APPARATUS AND ASSOCIATED METHOD

[75] Inventor: Fumihide Takeda, Minamiku, Japan

[73] Assignee: Takeda Engineering Consultant Inc., Japan

[*] Notice: The term of this patent shall not extend beyond the expiration date of Pat. No. 5,425,372.

[21] Appl. No.: 458,867

[22] Filed: Jun. 2, 1995

Related U.S. Application Data

[60] Division of Ser. No. 81,584, Jun. 22, 1993, Pat. No. 5,425,372, and a continuation-in-part of Ser. No. 509,029, Apr. 13, 1990, Pat. No. 5,222,020.

[51] Int. Cl.$^6$ ........................................................ A61B 5/00
[52] U.S. Cl. ........................ 128/672; 128/680; 128/681; 128/682; 128/687; 128/691
[58] Field of Search ........................... 128/668, 672, 128/677–683, 687, 690, 691, 748; 364/413.03

[56] References Cited

U.S. PATENT DOCUMENTS

| | | | |
|---|---|---|---|
| 4,651,747 | 3/1987 | Link | 128/677 |
| 4,718,428 | 1/1988 | Russell | 128/679 |
| 4,796,184 | 1/1989 | Bahr et al. | 364/413.03 |
| 5,222,020 | 6/1993 | Takeda | 364/413.03 |
| 5,425,372 | 6/1995 | Takeda | 128/672 |

OTHER PUBLICATIONS

Takeda et al, "A Clinical Monitoring of Arterial Wall Motion In Noninvasive Blood Pressure Measurements," accepted by the 7th International Conference on bioMedical Engineering, May 15, 1992.

Takeda et al, "A Simultaneous Monitoring of Brachial and Finger Arterial Wall Motions in Noninvasive Blood Pressure Measurements" accepted by the 7th International Conference on BioMedical Engineering on May 15, 1992.

Takeda et al, "Acquisition and Monitoring Methods of Arterial Wall Motion in Noninvasive Blood Pressure Measurements," Digest of the World Congress on Medical Physics and BioMedical Engineering, Medical and Biological Engineering and Computing, vol. 29, Supplement Part 1, 1994, 4 pages.

*Primary Examiner*—Robert L. Nasser, Jr.
*Attorney, Agent, or Firm*—Klarquist Sparkman Campbell Leigh & Whinston, LLP

[57] ABSTRACT

Using an improved noninvasive blood pressure measuring apparatus, dynamic parameters (like stretching and contracting velocity, acceleration, force, power and energy) of human arterial wall motion against both the lowering and increasing pressure of an occlusive cuff are detected. They can be displayed along with other physiological signals like aortic pressure AP and ECG taken from other instruments through a data receiving unit. Then this apparatus with ECG makes it possible to noninvasively detect some abnormalities between the mechanical and electrical cardiac cycle on heart function. The apparatus also detects systolic (SYS) and diastolic (DIA) pressure while increasing the cuff pressure. The apparatus can also examine a non-local information on blood circulation by simultaneously using a second occlusive cuff. Since this apparatus is capable of acquiring any physiological signal coupled with a commonly practiced noninvasive brachial artery blood pressure measurement, it will be also useful for quick and mass clinical testing.

5 Claims, 19 Drawing Sheets

FIG. 4
FIG. 5
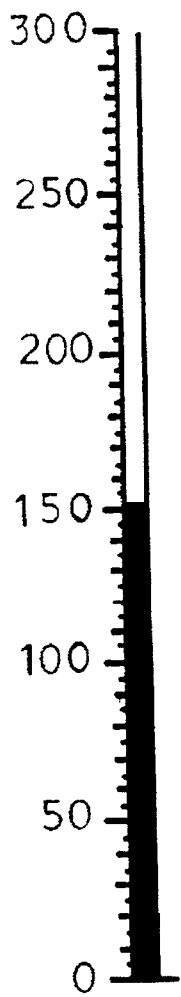
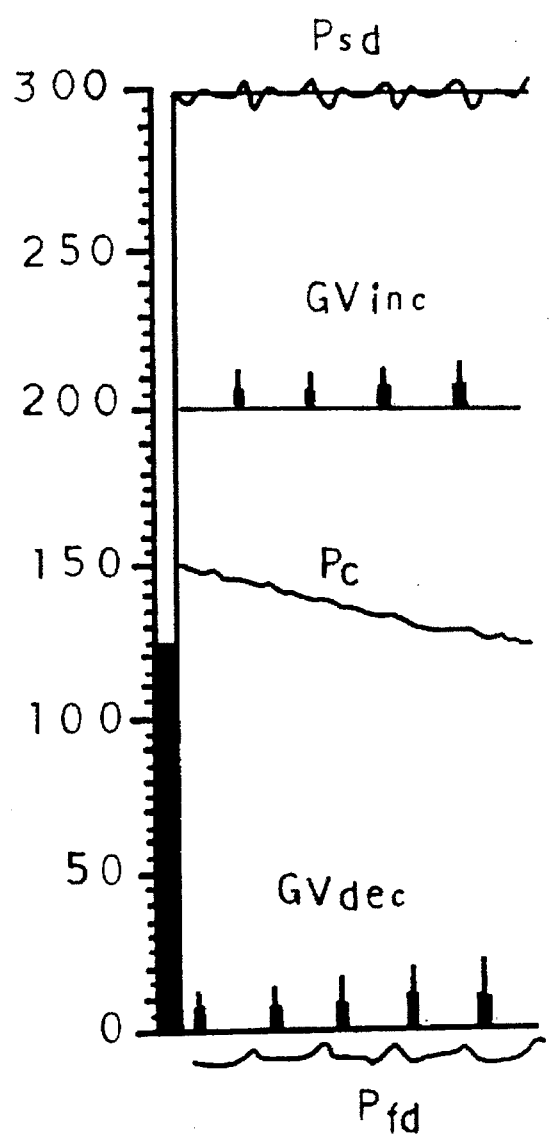

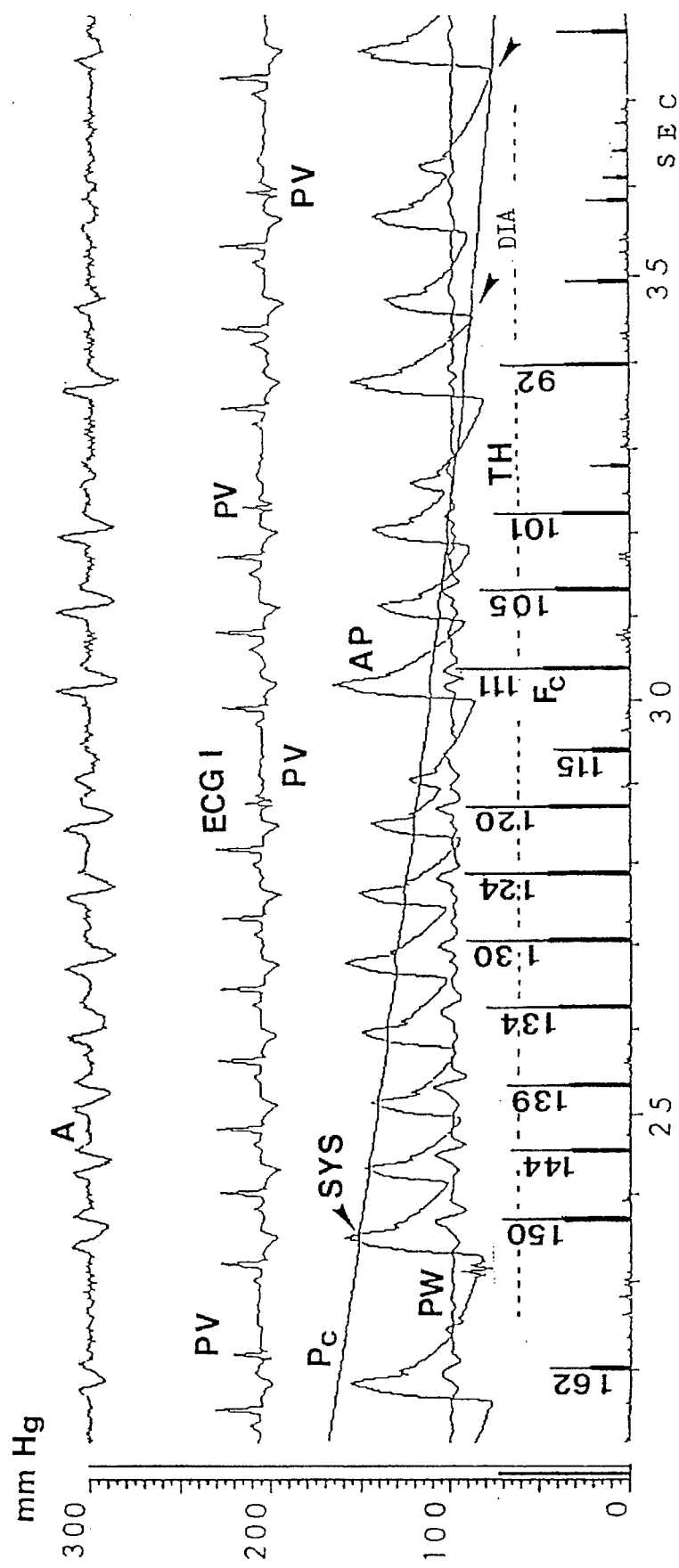
Fig. (8-a)

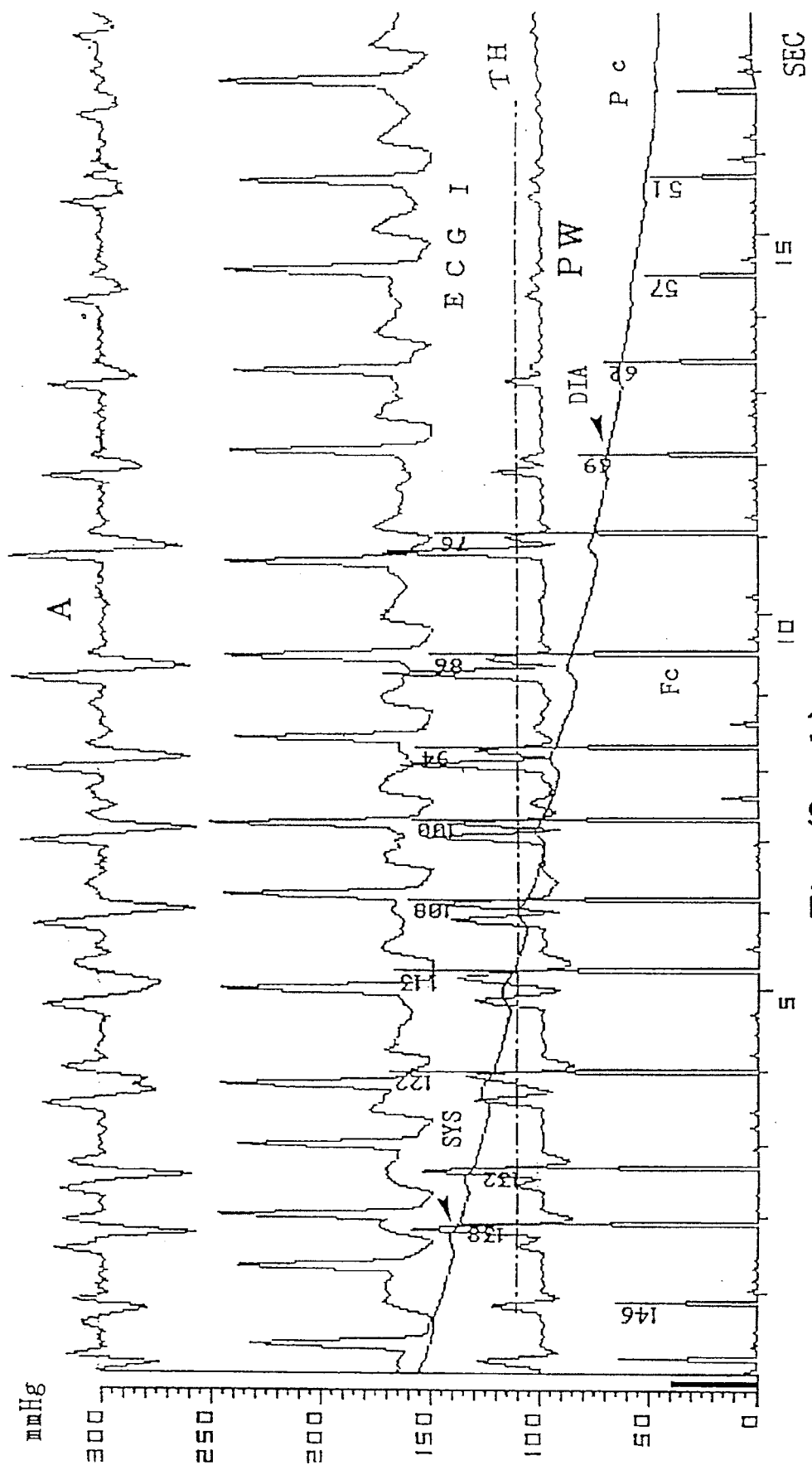
Fig. (8 - b)

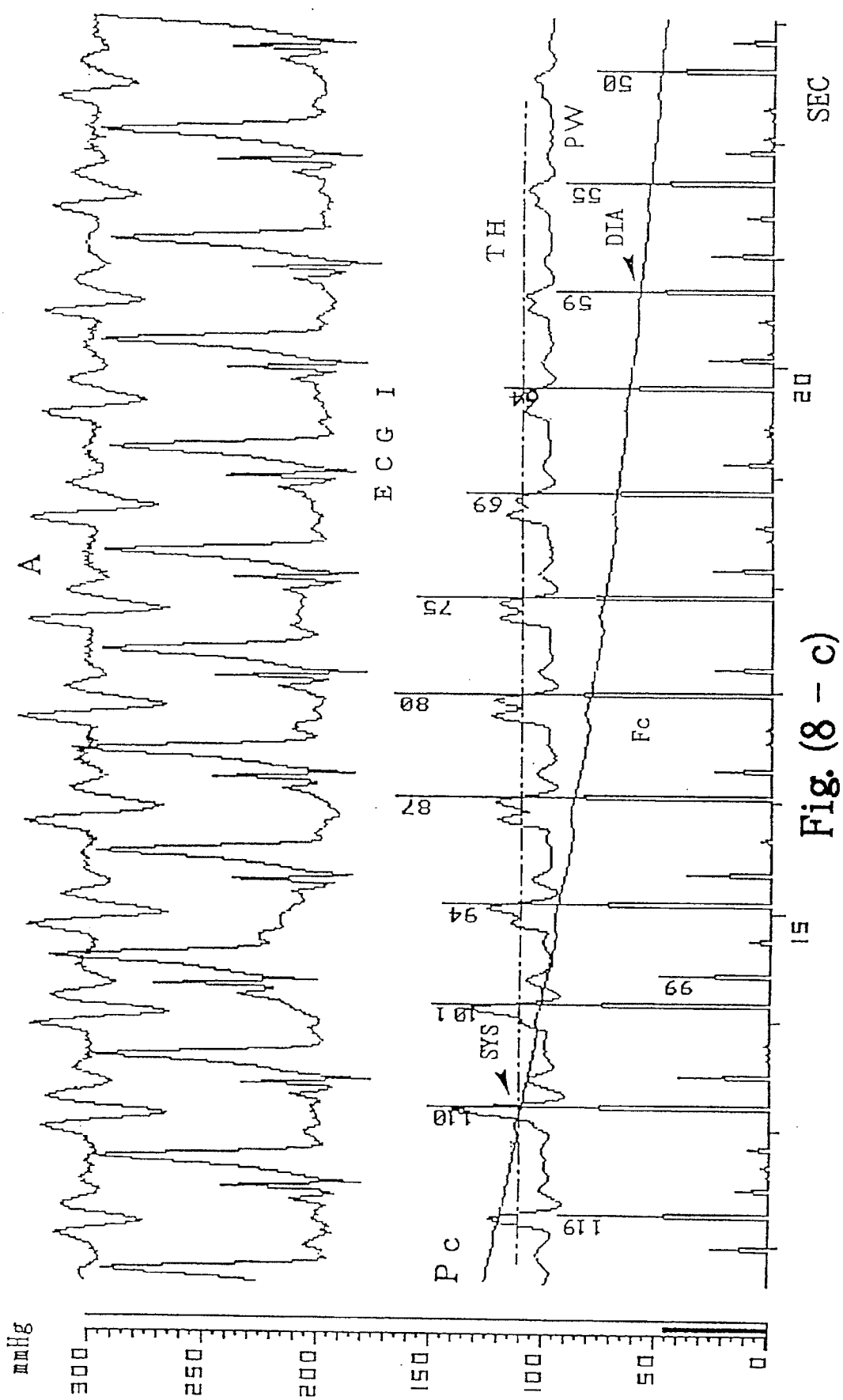
Fig. (8 - c)

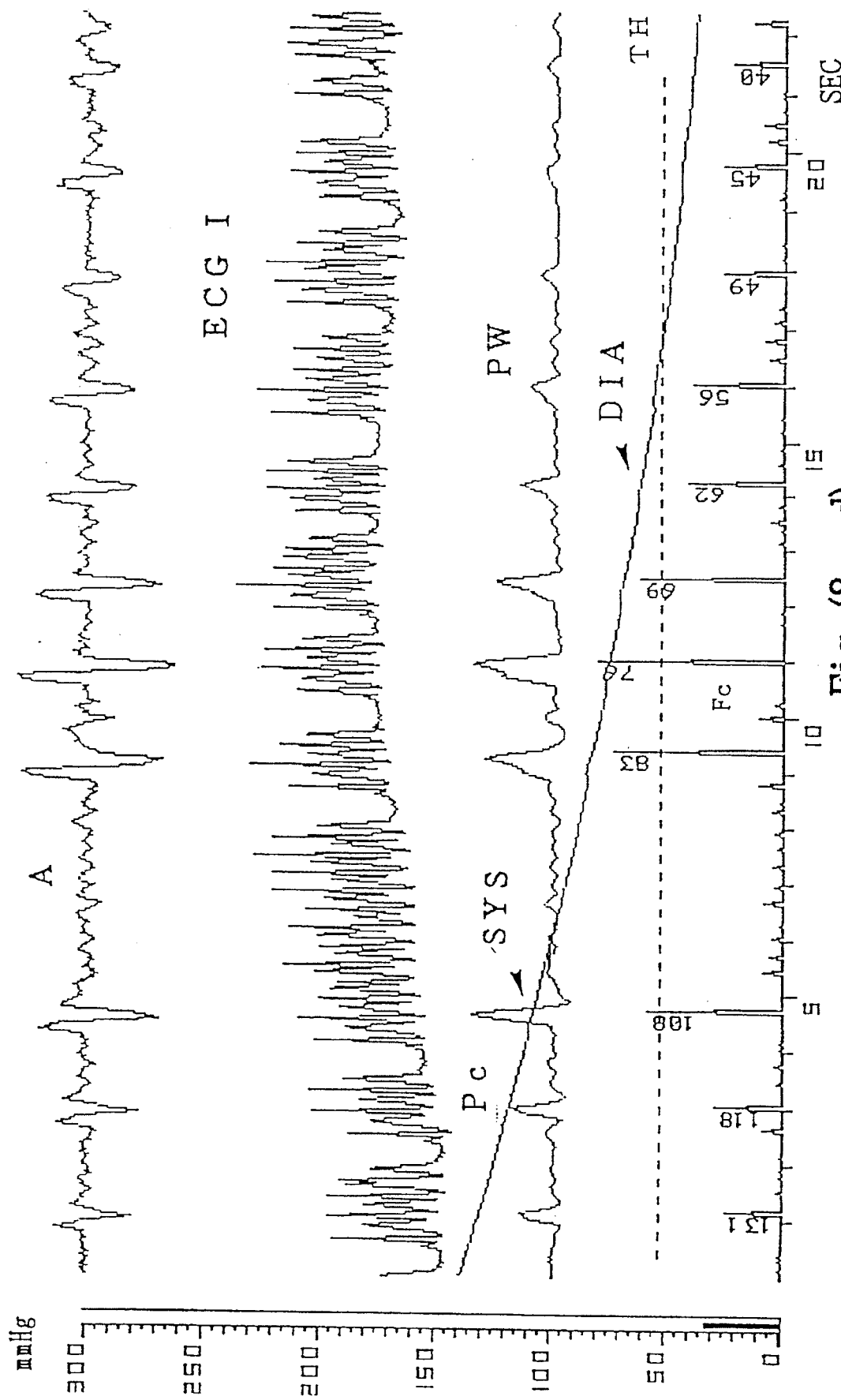
Fig. (8 - d)

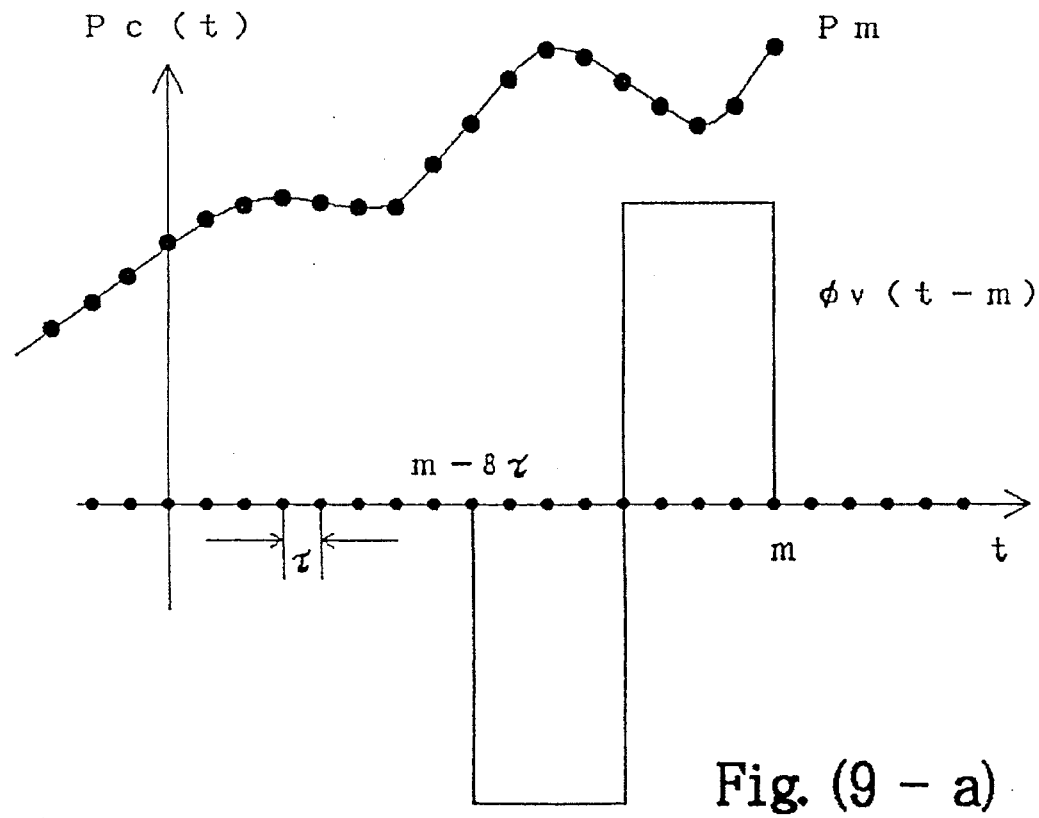
Fig. (9 – a)
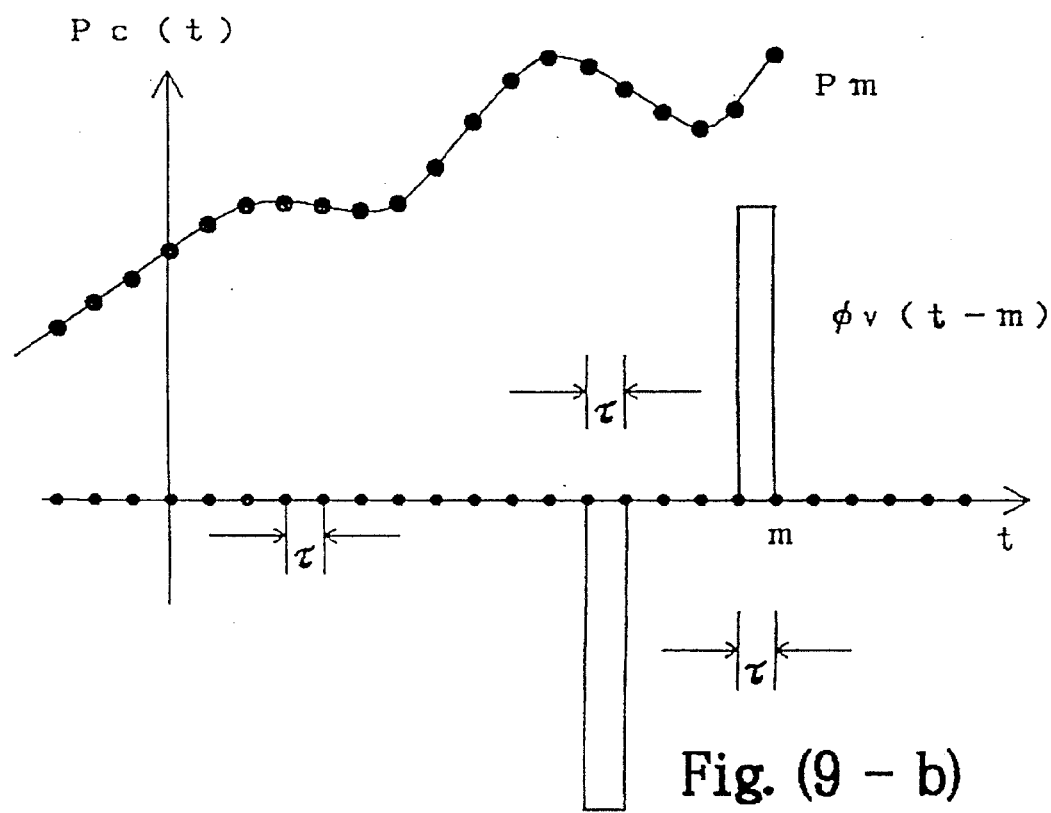
Fig. (9 – b)

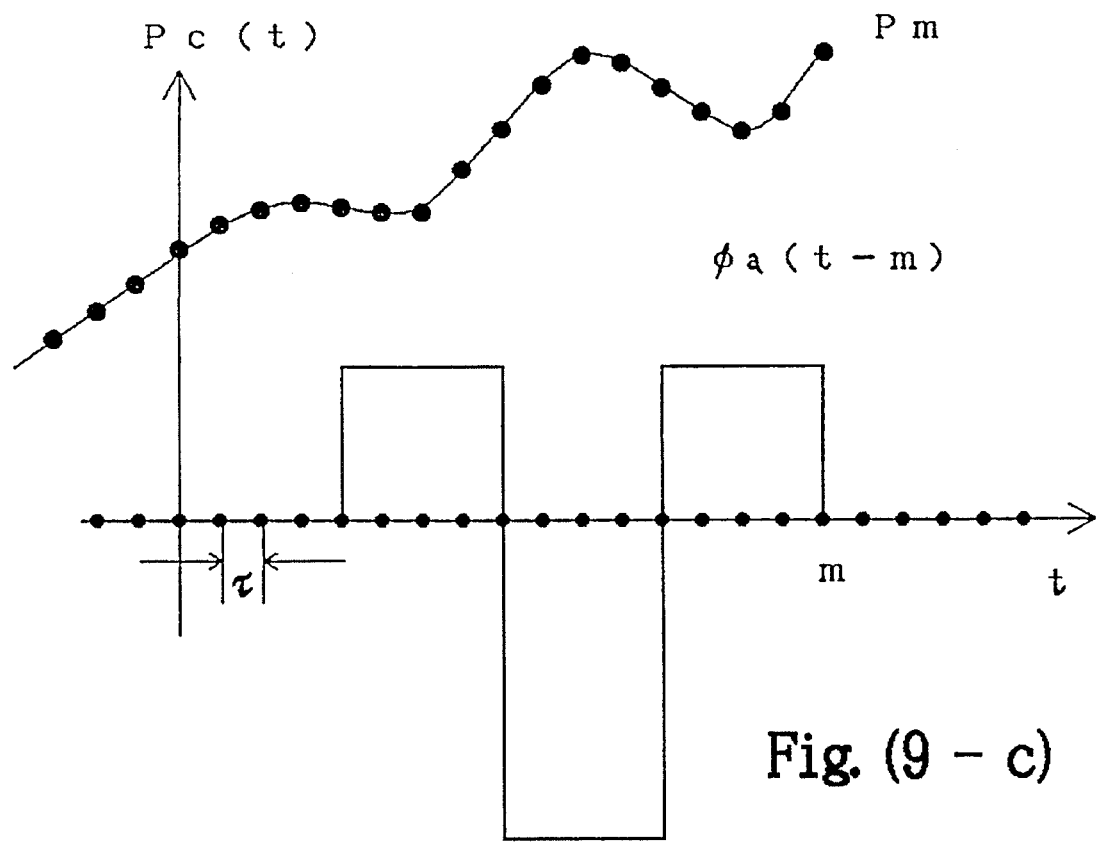
Fig. (9 - c)
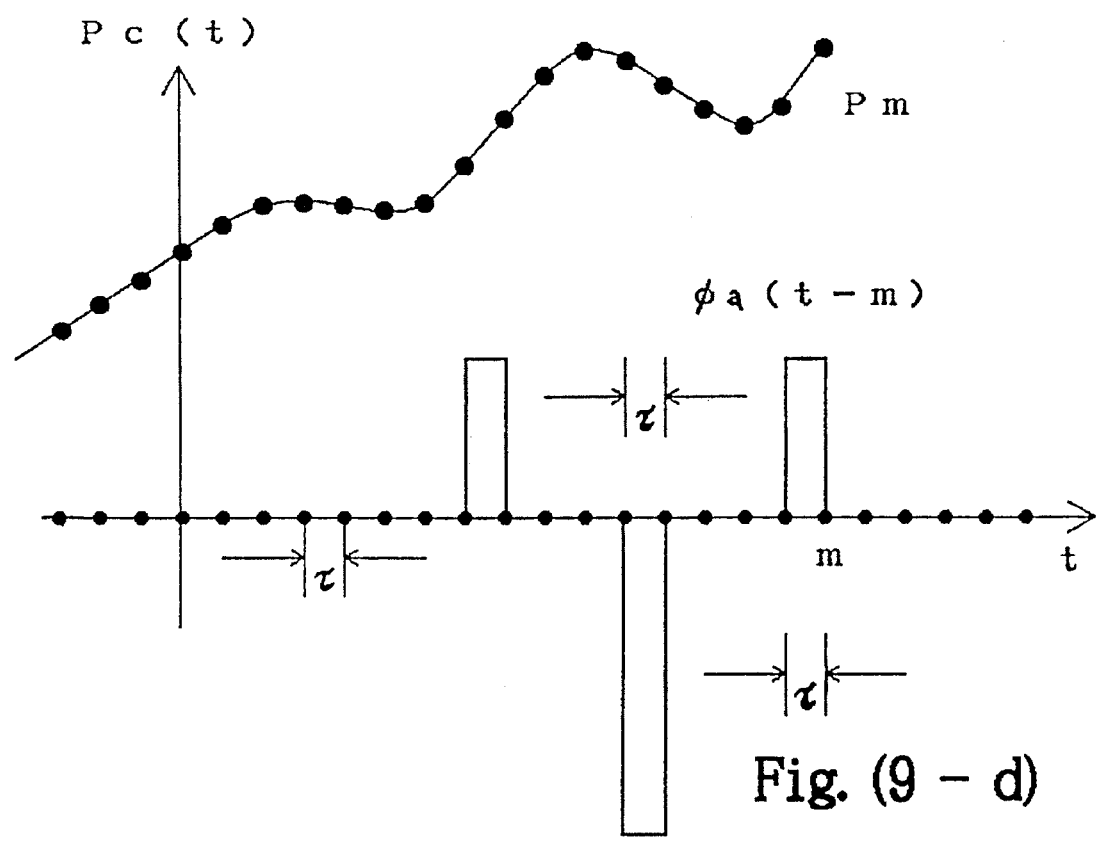
Fig. (9 - d)

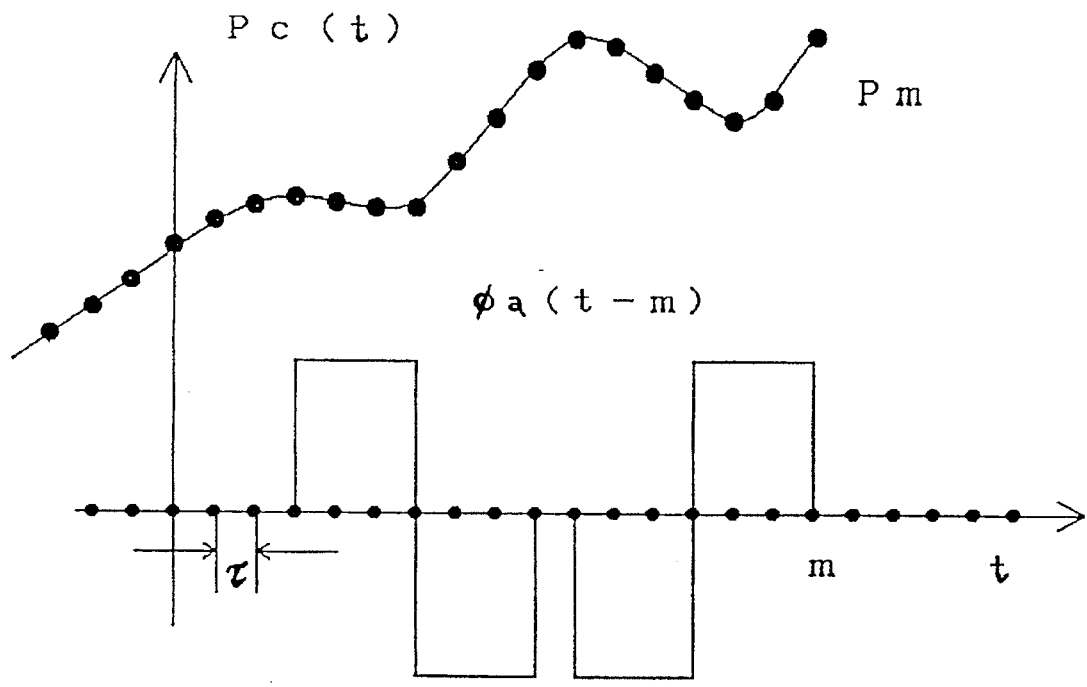
Fig. (9 − e)
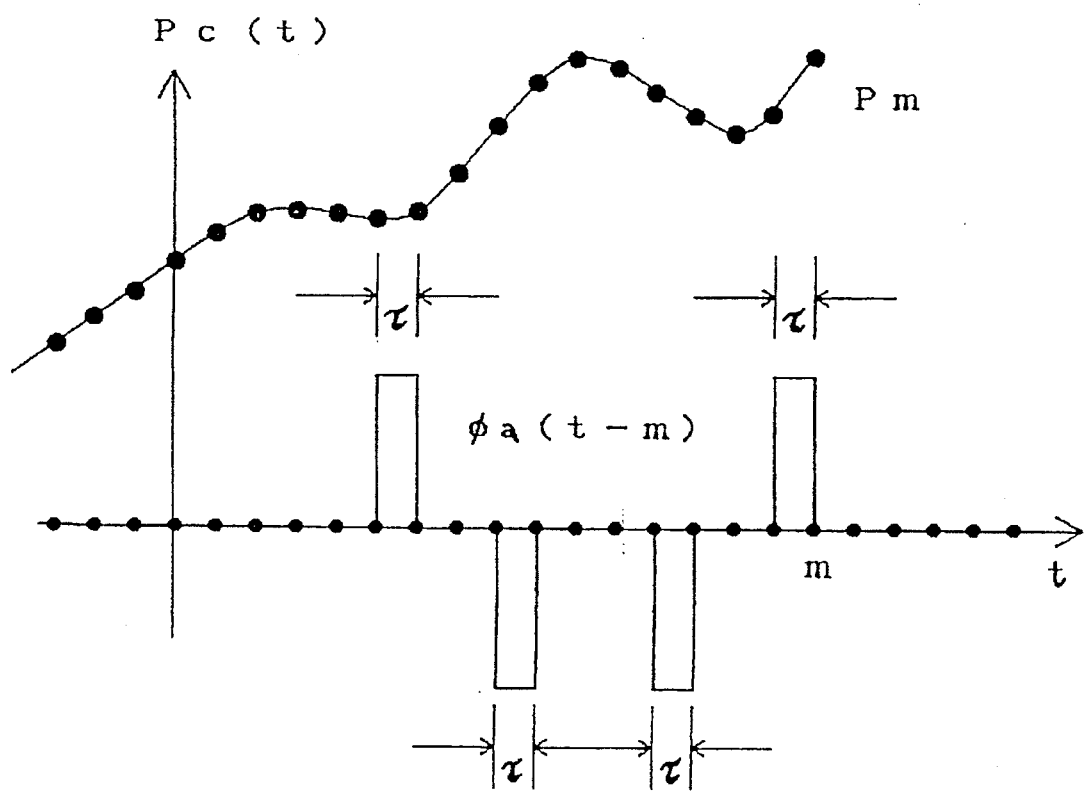
Fig. (9 − f)

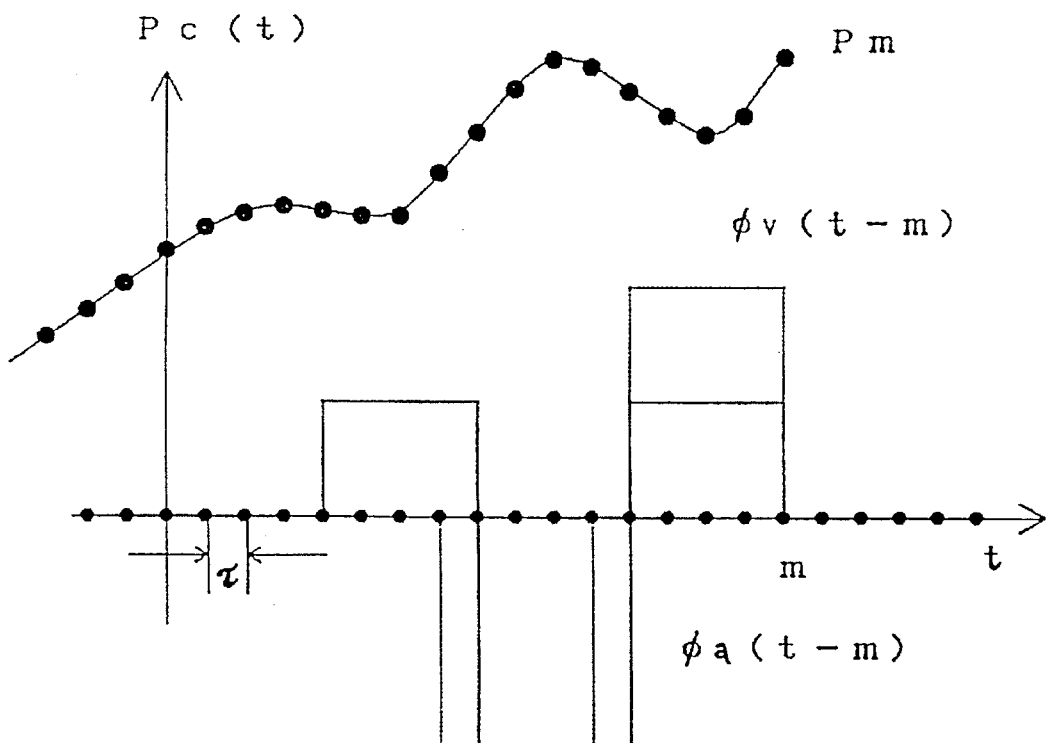
Fig. (9 – g)
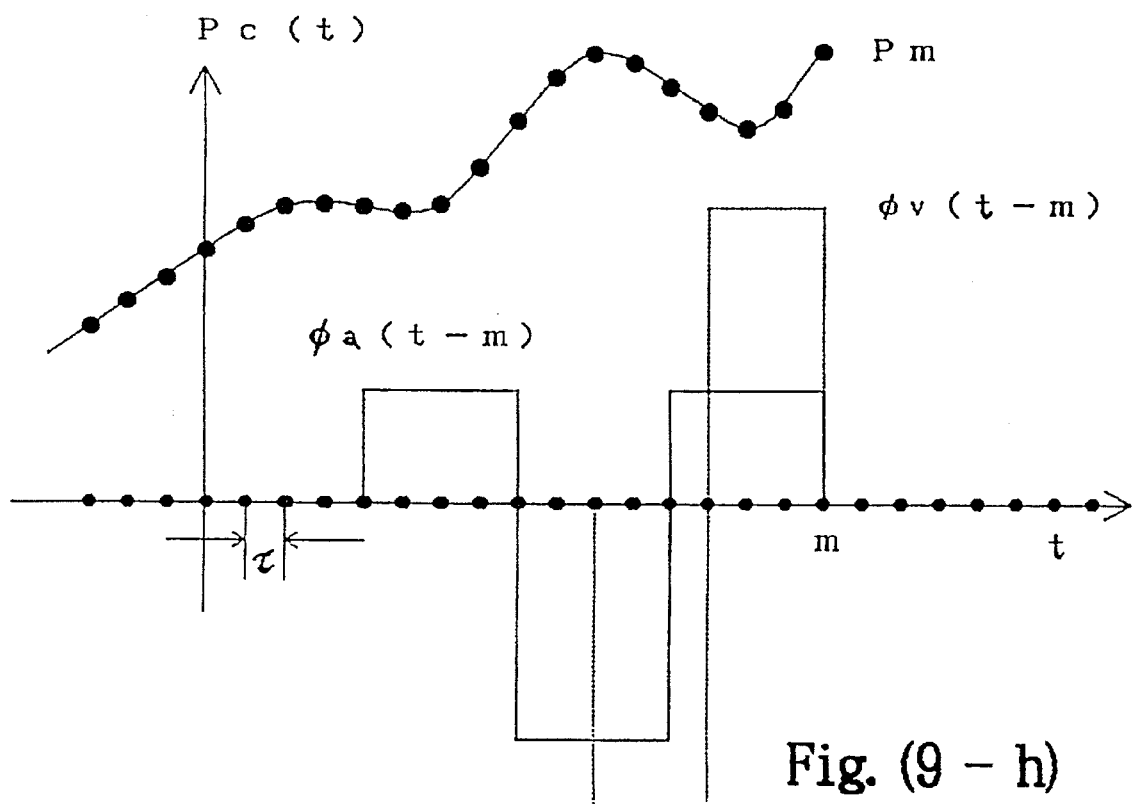
Fig. (9 – h)

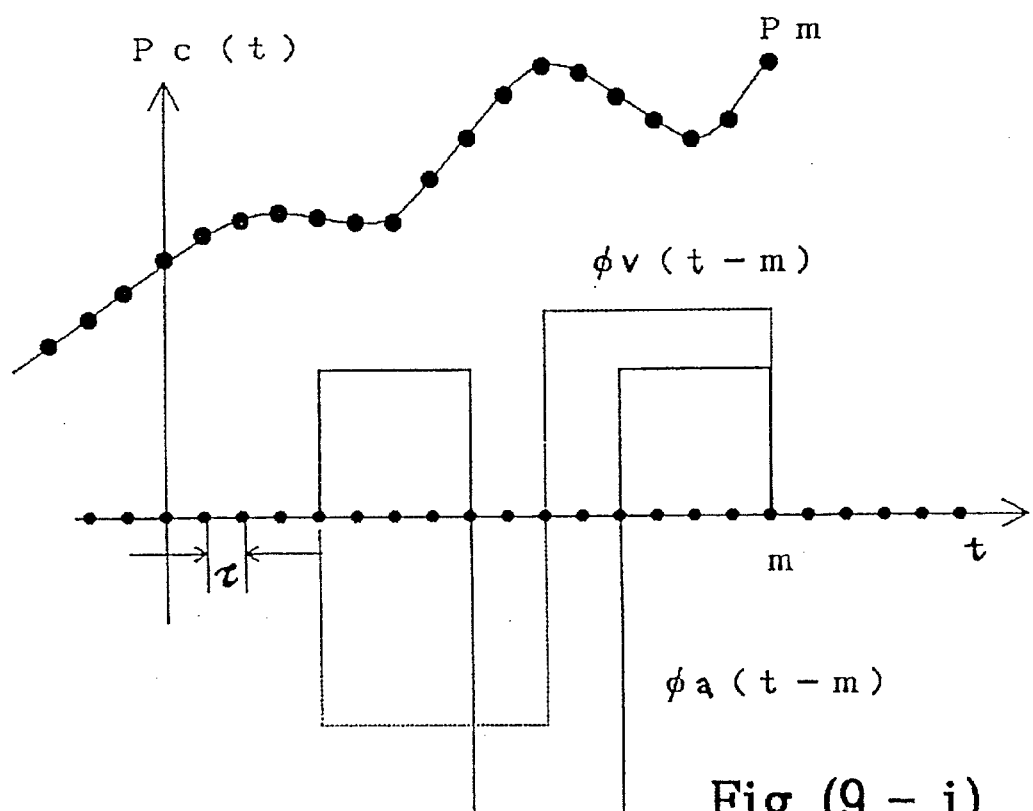
Fig. (9 – i)
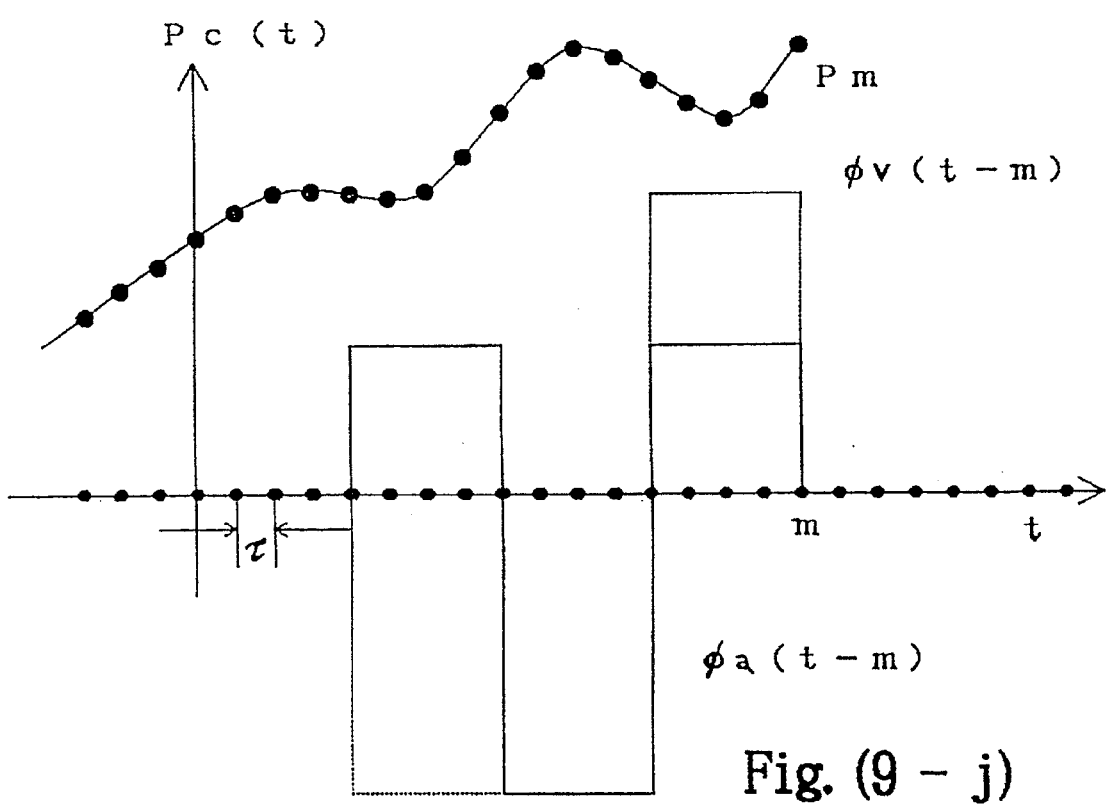
Fig. (9 – j)

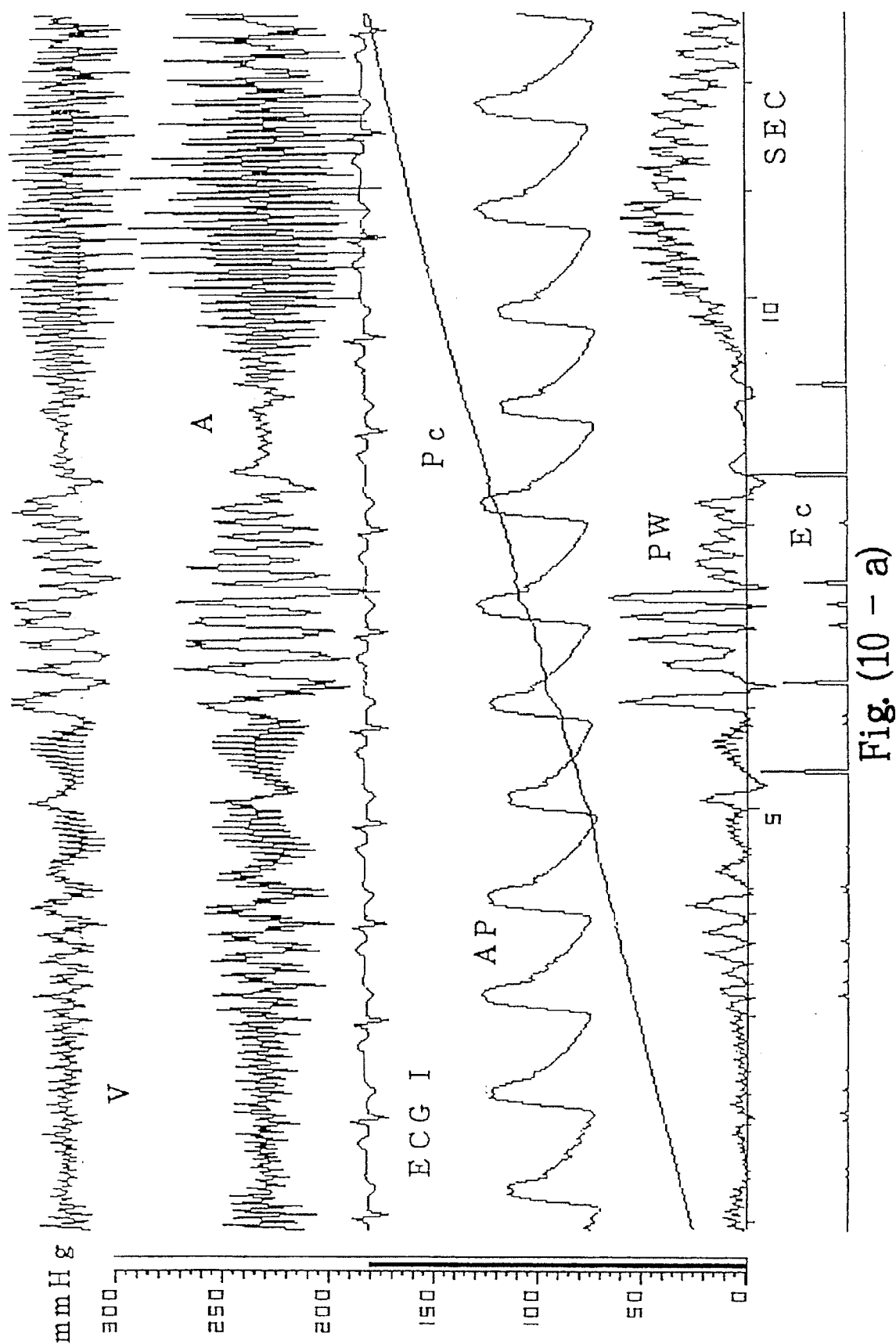
Fig. (10 – a)

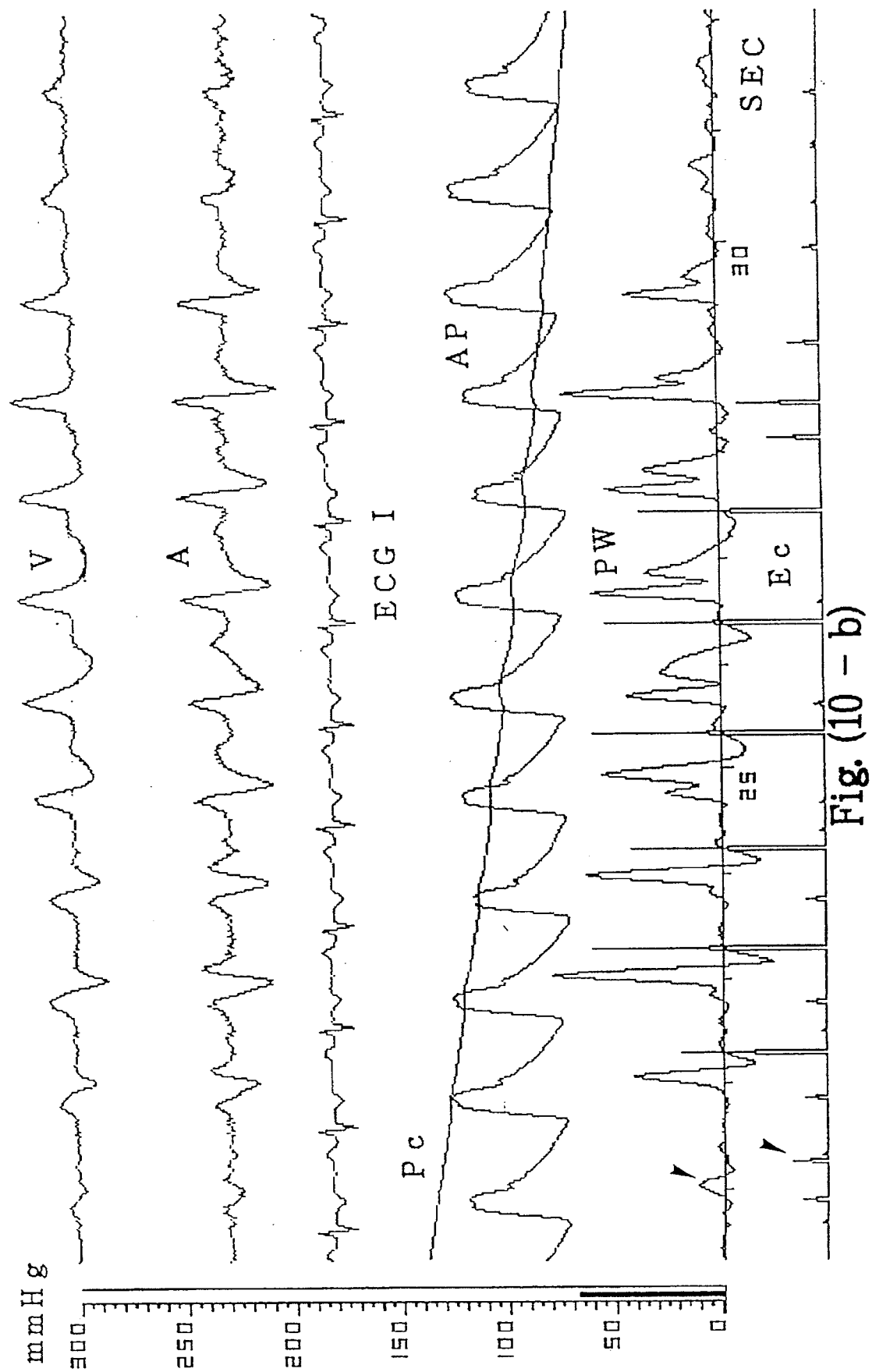
Fig. (10-b)

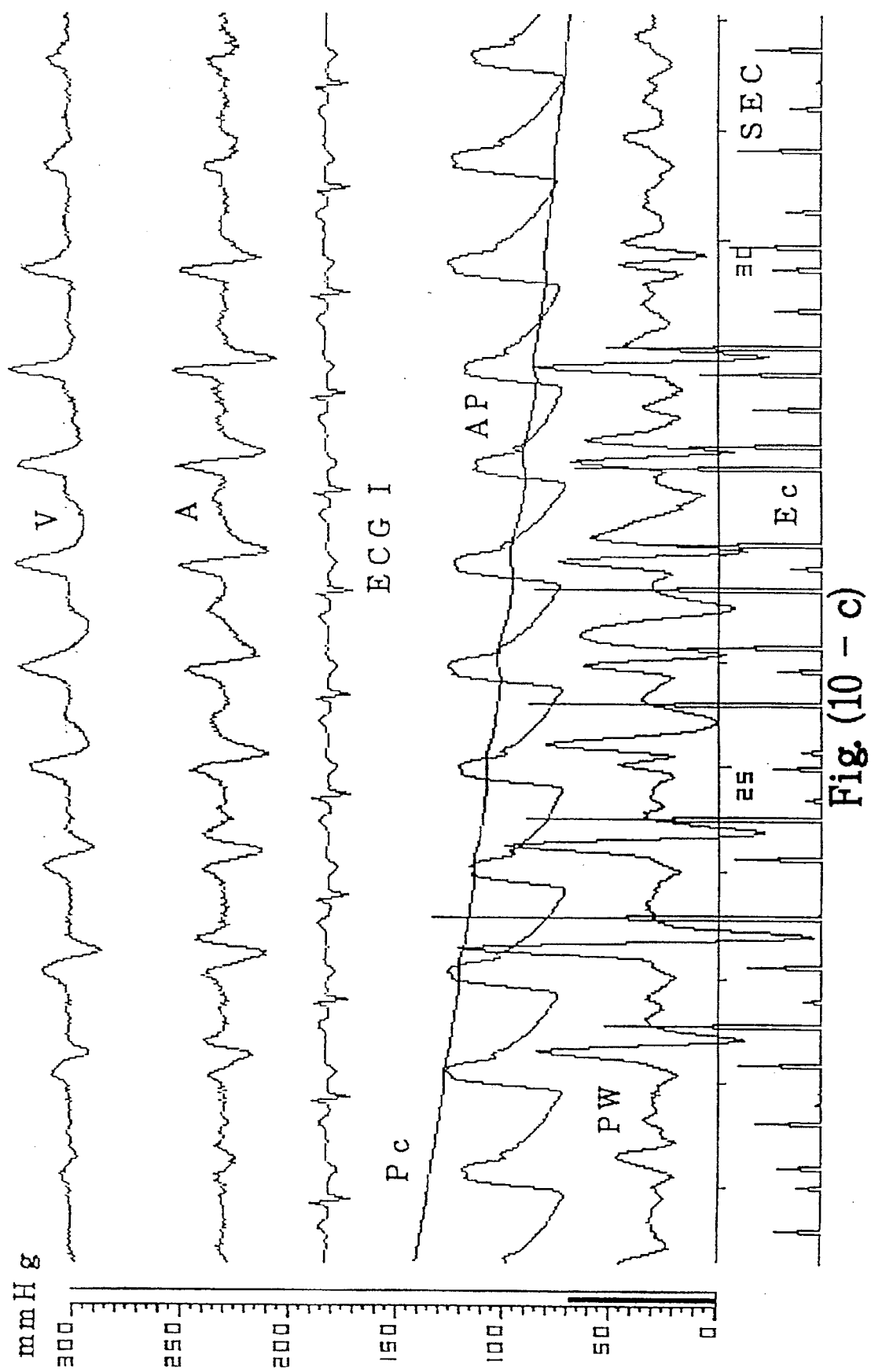
Fig. (10 - c)

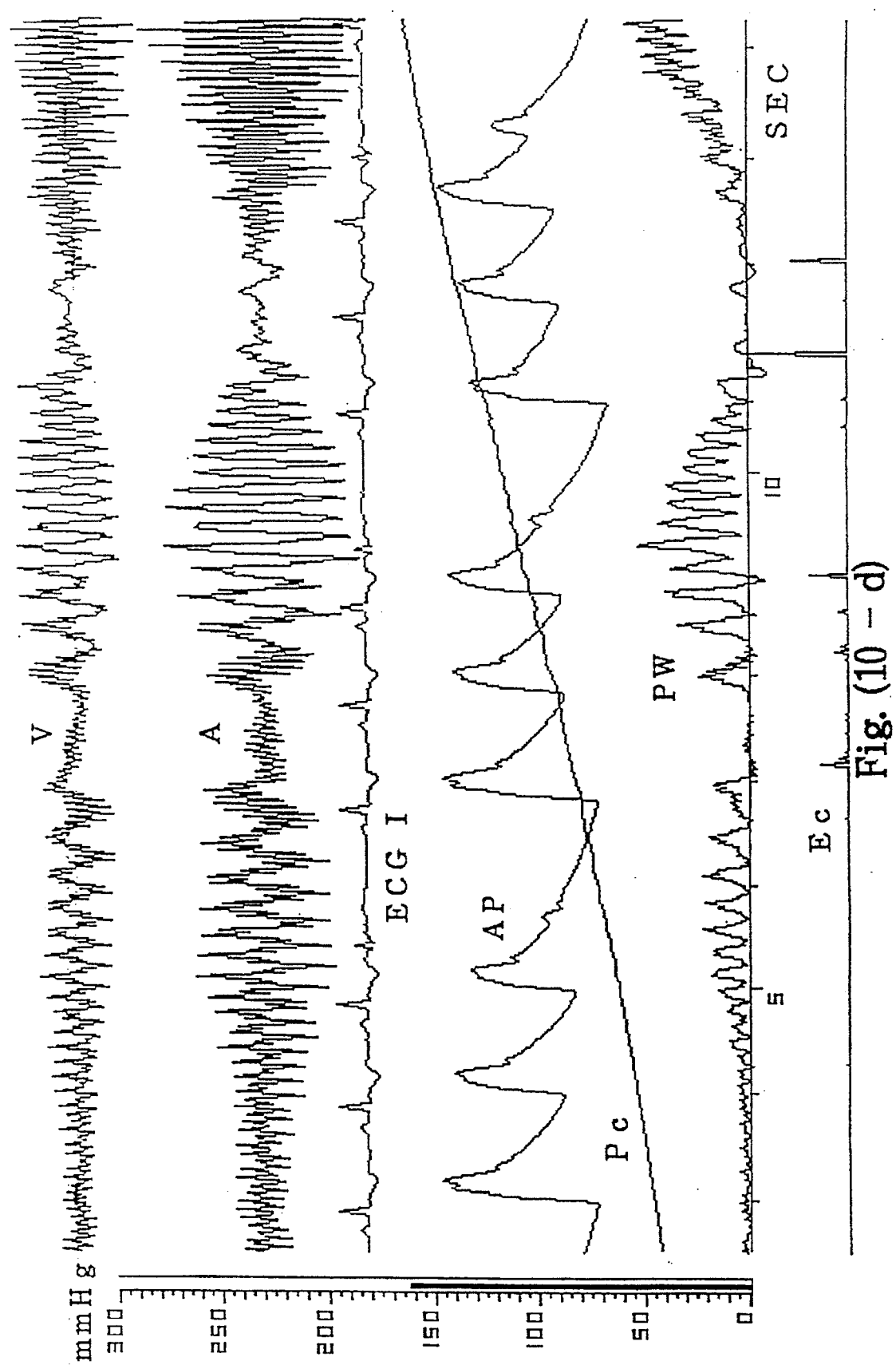
Fig. (10 − d)

BLOOD PRESSURE MEASUREMENT APPARATUS AND ASSOCIATED METHOD

RELATED APPLICATION DATA

This application is a divisional of U.S. patent application Ser. No. 08/081,584, filed Jun. 22, 1993, now U.S. Pat. No. 5,425,372, and a continuation-in-part of U.S. patent application Ser. No. 07/509,029, filed Apr. 13, 1990, now U.S. Pat. No. 5,222,020.

TECHNICAL FIELD

In the field of noninvasive blood pressure measurement using a cuff, pressurizing unit and bleeding valves, this invention relates to a method of acquiring a response to the pulsating blood flow which produces stretching of the arterial wall against the bleeding cuff's pressure. The method includes displaying the cuff's fluctuating pressure on a display unit in terms of a variation in the height of the mercury column of a mercury manometer. The arterial wall stretching includes that which occurs before and after each systolic and diastolic pressure detection and between the two detections. The invention further relates to a method of measuring blood pressure by monitoring and recording the arterial response.

Apparatus according to the invention can display the simulated motion of a needle indicator of an aneroid manometer in addition to displaying the mercury column. Thus, the invention does not require the manometers used previously in auscultatory methods. The invention can also graphically display in real time the arterial wall's subtle motion, which cannot be detected by the auscultatory method with a stethoscope and a microphone. The wall motion is displayed in the form of time varying physical quantities such as acceleration, velocity and the like. This invention can therefore be used as the auscultatory method while monitoring the information being displayed.

BACKGROUND OF THE INVENTION

For acquiring the arterial response to the pulsating blood flow by noninvasive blood pressure measurement with a cuff, a pressurizing unit and bleeding valves, there have been the following available methods: displaying only the intensity level of the Korotkoff's sounds graphically by using a microphone, and displaying the cuff's oscillating pressure wave whose constant bleeding rate is filtered out.

However, there do not exist blood pressure measurement devices which display, in real time, information on the response to the pulsating blood flow and the bleeding of the cuff's pressure while simultaneously displaying the simulated mercury and aneroid manometers.

The invention resolves the following problems of prior measurement devices. Using current methods with a microphone, the acquired dynamic response of an artery to pulsating blood flow does not include information on arterial wall motion. That undetected motion includes movement that creates and annihilates the Korotkoff's sounds, movement immediately before and after the sounds, and movement not creating any Korotkoff's sounds.

The response to the pulsating blood flow which is obtained with the AC component of the cuff's pressure after filtering its DC component can show only the trend of the magnitude variation of the cuff's pressure oscillation. But the response cannot show the dynamic expansion rate of the arterial wall. Furthermore, the arterial response to pulsating blood flow from which the systolic and the diastolic pressure are determined varies with the environment in which a subject is placed and the individual characteristics of the subject. Obtaining accurate systolic and diastolic readings for various subjects is difficult from judging only the trend of the magnitude of the cuff's pressure oscillation.

A method of acquiring the arterial response to pulsating blood flow is described in Japanese patent applications No. 61-118305 and No. 61-276785. The applications describe a filtering method. The method takes the first derivative of the cuff's pressure and then its integration with respect to time to obtain the increased amount of the cuff's pressure caused by the arterial expansion against the cuff's pressure. Thus, it merely increases the accuracy of the filtering of the oscillating pressure. Since this integration is carried on with the first derivatives above a constant threshold value, it is easily affected by a small change in the bleeding rate.

Difficulty often arises in displaying the graphics of the dynamic parameters characterizing the expansion of the arterial wall, namely the displacement velocity of the wall and the parameters related to its acceleration change.

Therefore, with the bleeding rate nearly constant or even changing, this invention acquires the time trend of the artery wall's expansion caused by the pressure fluctuation in pulsating blood flow against the cuff pressure, acquires the wall motion that gives the accurate systolic and diastolic pressure, and monitors the arterial response to the pulsating blood flow.

Another difficulty in noninvasive blood pressure measurements is obtaining the regulated constant bleeding rate and monitoring the change in the bleeding rate over time. In subjects, the detection of Korotkoff's sounds in phases 1, 4 or 5 often becomes difficult, depending on the magnitude of the bleeding rate. Furthermore, the physical and psychological surroundings of a subject alter one's normal systolic and diastolic pressure readings significantly. In these cases, medical personnel using current auscultatory blood pressure measuring methods have difficulty in determining the cause for the changes.

In U.S. Pat. No. 5,222,020, there is described a blood pressure measuring apparatus which is coupled with an occlusive cuff in order to acquire dynamics on a pulsatile wall motion of human artery responding to the occlusive cuff as its pressure is lowered. The instantaneous cuff pressure (Pc) is first obtained with a pressure transducer; then its value is displayed on a CRT in real time as height variations of mercury nanometer along with the dynamic parameters describing the pulsatile wall motion. The dynamic parameters are basically its displacement velocity and acceleration of the motion generated by blood flow pulsating against the lowering Pc, which reflects the mechanical cardiac cycle of heart as reported by F. Takeda, et al., in Med. Bio. Eng. Comput., Vol. 29, Supplement Part 1, 1991 which is hereby incorporated by reference.

In the commonly practiced noninvasive measurements with a pressure cuff and a bleeding valve controlling a quiet and constant deflation of cuff pressure Pc, without auscultation of Korotkoff sounds (KS) during their various phases, one may be obliged to use the oscillometric method to estimate systolic pressure (SYS), mean pressure (MEAN) and diastolic pressure (DIA) of human brachial artery. Its principle is that the oscillations of Pc which are transmitted by the arterial wall motion synchronizing with pulsatile artery blood pressure have their unique oscillation amplitudes (displacement amplitudes); for example, a sudden increase in their amplitudes when cuff pressure Pc unsynchronously gets to one of the arterial pressure pulse wave crests, their maximum amplitude, and a sudden decrease in their amplitudes when Pc unsynchronously approaches one of the pressure pulse wave troughs are used to detect SYS, MEAN and DIA, respectively, as reported by K. M. Borow et al., in Am. Heart J., Vol. 103, 1982. Since these sudden increases and decreases are very fuzzy, various techniques to determine SYS and DIA have been developed by T. W. Russell, described in U.S. Pat. No. 4,718,428, January 1988, D. E. Bahr et al., described in U.S. Pat. No. 4,796,184, January 1989, and Y. Miyawaki, et al., described in U.S. Pat. No. 4,793,360, December 1988.

As for detecting SYS and DIA in the present invention, no such analyses of fuzzy oscillation amplitudes are used. Instead, the dynamic parameters describing arterial wall motion are used. The use of some dynamic parameters to detect SYS and DIA will be made not only for quietly lowering Pc, but also for inflating Pc with a mechanical pump which produces noisy pressure fluctuations comparable with those due to arterial wall motion. This last feature to detect SYS while inflating Pc in automatic blood pressure measuring apparatus is very useful. This is because a pain which subjects often feel with the cuff pressure being inflated far above his or her own SYS can be greatly reduced.

Thus, one object of the invention is to resolve the difficulties stated above by displaying in real time the bleeding of the cuff's pressure during the blood pressure measurements as well as displaying the simulated mercury manometer.

A further object of the invention is the measuring and monitoring of the arterial response in nearly real time for those subjects remote from clinics or hospitals.

SUMMARY OF THE INVENTION

To achieve these objects, the cuff's pressure is deflated at nearly a constant rate through a bleeding valve. With an artery pressed by the cuff's pressure, the pressure fluctuation of the pulsating blood flow stretches the arterial wall and in turn the wall's stretching fluctuates the cuff's pressure.

To obtain the acceleration component of the fluctuating cuff's pressure $P_c$, the second derivative of $P_c$ is taken over the time interval for which the acceleration of the bleeding rate becomes nearly zero, even when the bleeding rate is not constant. The second derivative is denoted $P_{sd}$. To acquire $P_{sd}$ without it being influenced by the bleeding rate, the quantity proportional to the expansion displacement of the artery when pressed as stated above is taken with a displacement transducer such as an optical sensor or the like. Its second derivative with respect to time is then denoted by $P_{sd}$. Also, the quantity proportional to the displacement velocity of the artery is taken with a velocity transducer such as an ultrasonic sensor or the like placed. It is denoted $P_{fd}$. The first derivative of $P_{fd}$ is then denoted by $P_{sd}$. Thus, $P_{sd}$ may be obtained from two sources for verifying it value.

As for $P_c$, its mercury height's pressure in millimeters of mercury (mm Hg) is scaled on the Y-axis of a display and its time scale $T_c$ is given in seconds on the X-axis. As for the $P_{sd}$, its magnitude is arbitrarily enlarged on the Y-axis of $P_c$ and its time scale $T_{sd}$ is drawn on the X-axis of $P_c$.

The region surrounded by $P_{sd}$ and time axis $T_{sd}$ is subdivided by each intersection of $P_{sd}$ and $T_{sd}$, namely T1, T2, ..., Tm−1, Tm, Tm+1, and so on. Among them, the integral over the positive region, i.e., its area, is taken as the increased value of the wall's displacement velocity GVinc, and the area of its negative region is taken as the decreased value of the displacement velocity GVdec. Their magnitudes are respectively denoted by the length on a bar graph, namely L0, L1, etc. for GVinc and D0, D1, etc. for GVdec and so on. Their scale is enlarged on the $P_c$'s Y-axis as that of $P_{sd}$. Tinc and Tdec are the time scale for the GVinc and GVdec, respectfully, and their unit is seconds.

The mean accelerating force GAinc for stretching the artery wall is defined as the division of each amplitude (L and S), which is the amount of increase in GVinc, by the time duration for expanding the wall. The mean accelerating force GAdec for contracting the wall is defined as the division of each amplitude (D), which is the amount of decrease in GVdec, by the time duration of contracting the wall. Thus, the arterial response in terms of $P_c$, $P_{sd}$, GVinc, GVdec, GAinc and GAdec- may be graphically displayed.

The velocity component $P_{fd}$ may be obtained in a number of ways. It may be acquired by taking the first derivative of the cuff's pressure $P_c$ detected through a pressure transducer with acquiring $P_{sd}$ or it may be acquired directly through a transducer that detects the arterial wall motion.

Increases (L and S in GVinc) and decreases (D in GVdec) in the acceleration component $P_{sd}$ of the arterial wall motion may be acquired by taking the difference between velocity components at each intersection (T1, ... Tm). For example, L1 is proportional to $P_{fd}$(T2) minus $P_{fd}$(T1) and D1 is proportional to $P_{fd}$(T3) minus $P_{fd}$(T2). Dividing L,S and D by the time spent producing the change produce the mean expanding and contracting acceleration forces GAinc and GAdec, respectively.

Another object of this invention is to provide a method of measuring blood pressure which gives nearly the same systolic and diastolic pressure readings as those obtained by the auscultatory method. For that purpose, when the amplitude of GVdec becomes consecutively larger than its threshold (two-thirds of its maximum amplitude Dmax), the cuff pressure giving the closest amplitude to that threshold is taken as the systolic pressure SYS. Similarly, when the amplitude of GVdec becomes consecutively smaller than its threshold, the cuff pressure giving the closest amplitude to the threshold is taken as the diastolic pressure DIA.

This invention also provides a method of measuring blood pressure which gives the accurate systolic and diastolic pressure readings by using the unique wave form of the acceleration component $P_{sd}$. The systolic pressure is transformed either into the change in time ΔTm between Lm and Sm (where m=1,2,3) in the increased displacement velocity component GVinc on the wall, or their amplitudes' change Δm and so on. The cuff pressure is taken as the systolic reading SYS at the time the uniqueness is found for which either of ΔTm and Δm or both start to increase. Furthermore, the mean value of the amplitudes D1 (at SYS), D0 (immediately before SYS) and D2 (immediately after SYS) is obtained. The cuff pressure at the time the decreased displacement velocity component GVdec on the wall becomes smaller than Dave or D1 is defined as the diastolic pressure reading DIA.

Another object of the invention is to provide a noninvasive blood pressure measuring apparatus comprising a cuff and tubes which can be wrapped around an artery in a finger, arm or a leg to be pressed; pressurizing and bleeding units for inflating the cuff and tubes; a pressure transducer for detecting the cuff's pressure; a displacement transducer for detecting displacement of the arterial wall motion; a velocity transducer for detecting a displacement velocity of the motion; a micro-controller for controlling each unit; a data processor and memory unit for carrying out the methods described; a display unit for showing the process data; and a data transmission unit.

With this apparatus, the fluctuating pressure reading acquired through the pressure transducer is displayed in real time as the height of a mercury column in the manometer glass tube. Then the cuff pressure on the subject's artery is raised a little above the systolic pressure before deflation. Setting the time axis at an arbitrary position, there are simultaneously displayed in real time the trend of the cuff's pressure $P_c$, the acceleration of the arterial wall's displacement $P_{sd}$, and the increased and decreased amount of GVinc and GVdec, and the time trend of GAinc, GAdec and $P_{fd}$.

There are also displayed Dmax, threshold Dmax-⅔ being calculated with Dmax, and D1. Thus, this apparatus measures the blood pressure non-invasively while monitoring the arterial response, and transmits the acquired data to other instruments through a network, a telemeter or the like.

The invention displays in real time the instantaneous velocity and acceleration of the arterial wall displacement which is obtained from fluctuations in the cuff's pressure. The invention also displays, in real time, the trend of the wall velocity change, and the characteristics of the time trend of the mean acceleration change.

The invention also displays in real time various wall expansion motions until the artery that is being pressed by the cuff's pressure relaxes to being free. Thus, with the displayed arterial wall motion the invention acquires the following: the abnormal wall expansion of the arterial wall that can not be detected by the Korotkoff's sounds; the small abnormality accompanying a light irregular heart beat or the like; and the change in the arterial response due an unusual psychological and physical environment in which the subject is placed (for example under alert conditions, after exercising and under the alcoholic influence). In particular, the visualized displacement acceleration that is acquired by this invention is able to easily differentiate the noise created by non-arterial wall motion. The pressure reading acquired with the pressure transducer is converted to the height of the mercury column. It is displayed in real time inside the glass tube and is stored in memory. Thus, even if this method is used along with an auscultatory method, it not only makes the detection of the Korotkoff's sounds in phases 1, 4 and 5 more certain, but also simplifies analyzing and storing the data in a way that can not be achieved by the blood pressure measurement techniques commonly practiced with mercury or aneroid manometers. Furthermore, transmission of the acquired data through a network or a telemeter is easily done.

The time changes of $P_{sd}$, GVinc, GVdec, GAinc and GAdec describe the expansion motion of the arterial wall. These changes may be used to noninvasively acquire information for the human cardiovascular system such as the degree of artery hardening and the like. Since apparatus according to the invention may also transmit the acquired data, measurements for subjects in remote locations can be monitored through a telephone hook-up. Medical personnel at the other end of the telephone line can instantaneously send appropriate instruction for treatment back to the subject through the apparatus.

If this apparatus is simultaneously used with an electrocardiograph, brain wave monitor or other instrument, the data obtained from these instruments can be displayed with the arterial response. Thus, the apparatus not only increases the added value on such instruments, but also allows the data to be combined with other data.

$P_{sd}$ can alternatively be obtained by time-differentiation of the wall displacement and the displacement velocity acquired during noninvasive blood pressure measurement with optical and ultrasonic transducers, respectively. Thus, the invention works with blood pressure measuring methods that use displacement and displacement velocity transducers.

In another embodiment, the invention uses a second cuff simultaneously in order to acquire a non-local information on arterial wall motion.

A wall motion of finger artery whose blood flow is circulated through the brachial artery partially occluded by the Pfc is shown along with cuff pressure Pc for brachial artery.

The invention also displays other physiological signals like ECG which triggers the mechanical cardiac cycles in order to examine if there exists abnormal correlation between the electrical and the mechanical event on heart.

Intra-arterial aortic pressure AP and ECG I are taken, and these physiological signals can be fed through a date receiving unit from other instruments. A normal and a few abnormal examples of clinical tests using this feature are shown and described in the specification.

The invention further obtains and displays other dynamic parameters describing arterial wall motion in order to noninvasively estimate the systolic (SYS) and diastolic pressure (DIA) of pulsatile artery pressure during both the inflation and deflation of cuff pressure (Pc).

The dynamic parameters describing the arterial wall motion include:

the instantaneous displacement velocity V which is to be obtained either by a first time derivative of cuff pressure Pc or with a velocity detection function;

acceleration A obtained either by a second time derivative of Pc or with an acceleration detection function;

each net compression shown as impulses Fc whose magnitude is proportional to the integral of negative A;

power PW of the wall motion defined as the product of A and V; and energy Ec compressing the arterial wall which is the integral of negative PW energy Es stretching the arterial wall which is the integral of positive PW.

SYS and DYA may be determined by using Fc. Fc is checked to see if it is under a partial constraint for which the pulsatile blood flow has to go through artery vessel partially occluded by the Pc. The threshold level for this partial occlusion is the dotted line TH whose value is two-thirds of the maximum Fc. This is because the maximum interaction with the cuff pressure will occur as the continuously lowering Pc gets to about mean arterial pulse pressure which is approximately at two-thirds of its amplitude from its peak. The arterial wall motion with Fc below TH is free from any partial occlusion so that it can not create KS. Thus, the determination of SYS and DIA becomes quite accurate.

Similarly, using other dynamic parameters like PW, Ec and Es, they are checked to see if they are under a partial constraint for which the pulsatile blood flow has to go through artery vessel partially occluded by the Pc. Their threshold levels for this partial occlusion can be set in a way analogous to the threshold line TH. The use of Ec is unique as will be seen. This is because the compressing energy detected with the velocity and acceleration detection function will be significant only for the partial constraint. This partial constraint starts as the continuously increasing Pc (or lowering Pc) approaches about diastolic pulse pressure (or systolic pulse pressure) and ends as the increasing Pc (or lowering Pc) approaches about systolic pulse pressure (or diastolic pulse pressure). The arterial wall motion free from any partial occlusion can not create significant Ec; namely negative PW. This holds for positive PW and Es as well. To see this process more clearly, aorta pulsatile blood pressure AP was invasively taken with a pressure transducer on a catheter, which expresses the mechanical cardiac cycle of heart.

Thus, the determination of SYS and DIA is quite accurate even for a noisy inflation process.

BRIEF DESCRIPTION OF THE DRAWINGS

FIG. 4 is a display of a simulated mercury manometer.

FIG. 5 is a display of the arterial response about five seconds after starting the blood pressure measurement.

FIG. 8-a is a display of a cardiac mechanical cycle which is normally triggered by the electrical cycle.

FIG. 8-b is a display of the arterial response showing the QRS peaks on the ECG I signal.

FIG. 8-c is a display of the arterial response showing how the side pulses accompanying the main FC's correspond with systolic murmur created with the aortic valve.

FIG. 8-d is a display of how an arterial fibrillation which appears too rapid for ventricular systoles to be triggered causes an irregular heart beat.

FIGS. 9-a through 9-j graphically show velocity and acceleration detection functions and power detection in accordance with the invention.

FIG. 10-a is a display of a time history of the parameter PW taken with the power detection function shown in FIG. 9-g.

FIG. 10-b is a display showing a continuation of the measurement begun in FIG. 10-a.

FIG. 10-c is a display of the same data shown in FIG. 10-b except for the parameter PW which is now taken with a different pair of detecting functions shown in FIG. 9-j to magnify the negative region of PW.

FIG. 10d is a display showing that Ec clearly detects DIA and SYS during a noisy auto-inflation process.

DETAILED DESCRIPTION OF PREFERRED EMBODIMENTS

Figure 1:
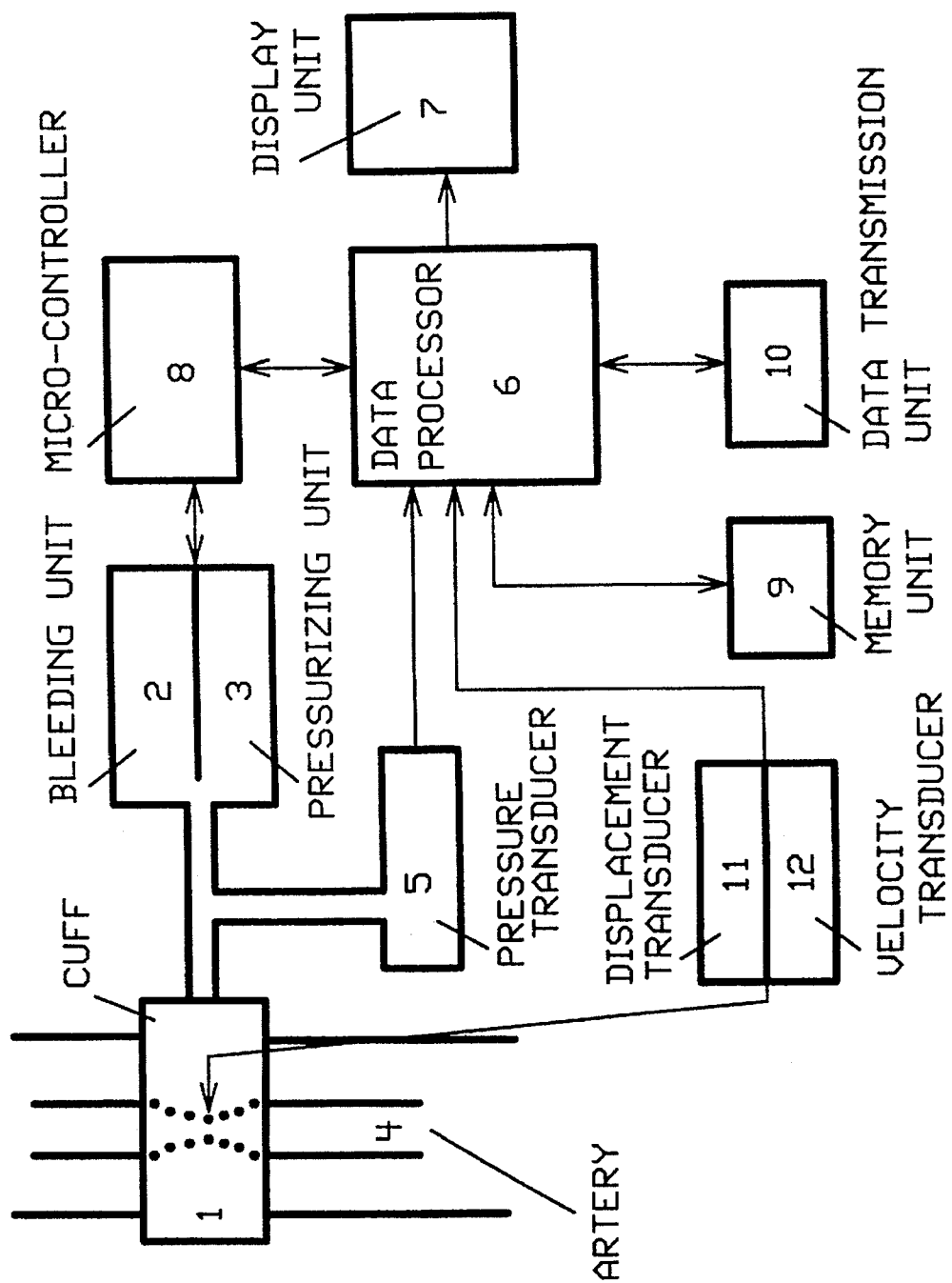
FIG. 1 is a block diagram of a first embodiment of an apparatus according to the invention for making noninvasive blood pressure measurements.

Referring now to FIG. 1, there is shown a first embodiment of a noninvasive blood pressure measuring apparatus according to the invention. The apparatus comprises a cuff 1 with embedded tubes which may be wrapped around an artery 4 within a finger, arm or leg. Connected to the cuff 1 are pressurizing and bleeding units 3 and 2 to inflate and deflate the tubes of cuff 1, respectively. A pressure transducer 5 is connected to the cuff for detecting the cuff's pressure as it is inflated and deflated and for communicating the pressure data as an electrical signal to a data processor 6. A displacement transducer 11 such as an optical sensor is connected to the cuff 1 for detecting the displacement of the arterial wall as it expands in response to the pulsating blood flow. A velocity transducer 12 such as an ultrasonic sensor is connected to the cuff 1 for detecting the velocity of the wall expansion. Transducers 11 and 12 communicate their respective data as electrical signals to the data processor 6.

The operation of the measuring apparatus is coordinated by a micro-controller 8 which controls the pressurizing unit 3, the bleeding unit 2 and the data processor 6. Data obtained from transducers 5, 11 and 12 and processed by data processor 6 may be stored in memory unit 9 and displayed on display unit 7. A data transmission unit 10 is also included in the apparatus. The unit 10 allows the acquired data to be transmitted to other instruments either directly or over the telephone lines and to receive data in return.

With the cuff inflated to a pressure $P_c$ by pressurizing unit 3, the artery 4 is squeezed by the cuff's pressure $P_c$. The pressure $P_c$ in the cuff is then deflated at nearly a constant bleeding rate through the bleeding valve unit 2. Against the artery 4, the pressure fluctuating of the pulsating blood flow starts to stretch the arterial wall which in turn moves to fluctuate the cuff's pressure.

Figure 2:
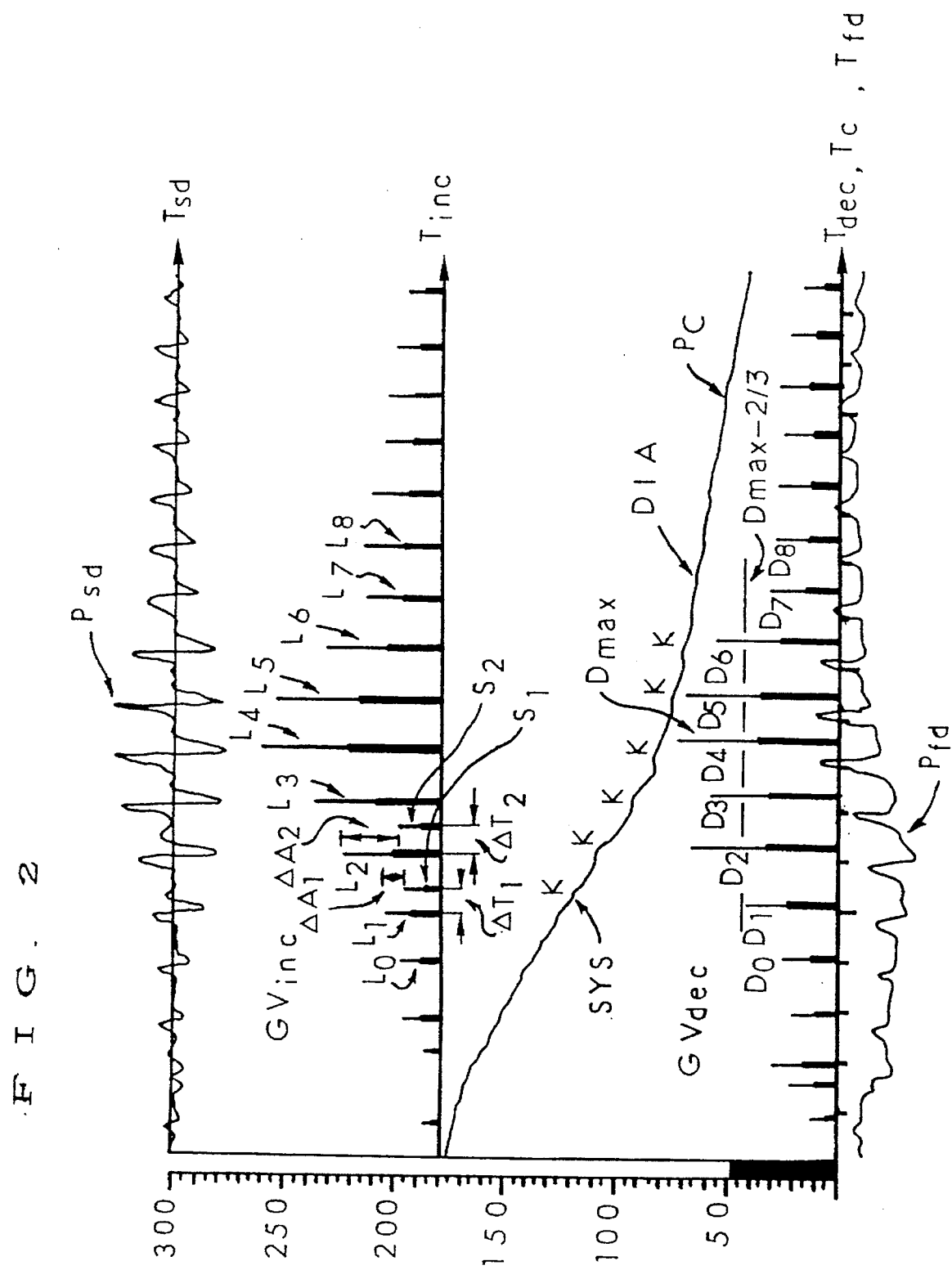
FIG. 2 is a display of the arterial response when the cuff's pressure's bleeding rate is fast and changing.

To obtain only the acceleration component of the fluctuating cuff's pressure $P_c$, the second derivative $P_{sd}$ of $P_c$ is taken at the data processing unit 6 over the time interval for which the acceleration of the bleeding rate becomes nearly zero. The relationship between $P_c$ and $P_{sd}$ is shown in FIG. 2 where the bleeding rate is not constant and in FIG. 3 where the bleeding rate is nearly a constant rate.

To acquire $P_{sd}$ without it being influenced by the bleeding rate, the quantity proportional to the wall's displacement of artery 4 pressed as stated above is taken with displacement transducer 11. Its second derivative with respect to time is denoted by $P_{sd}$. Also, the quantity proportional to the wall's displacement velocity of artery 4 is directly taken with velocity transducer 12 placed on the cuff. It is denoted by $P_{fd}$. The first derivative of $P_{fd}$ is $P_{sd}$. The numerical values processed at the data processing unit 6 are displayed on the displaying unit 7.

To display $P_c$, the pressure is simulated as the mercury height in mmHg at the display unit 7 with the Y-axis being pressure in mmHg and the X-axis being its time scale Tc in seconds. To display $P_{sd}$, its magnitude is enlarged on the Y-axis and its time scale $T_{sd}$ is arbitrary drawn at 300 on the Y-axis. The pressure fluctuation of Pc due to the pulsating blood flow is enlarged on $P_{sd}$ without being influenced by the bleeding rate where the subjects in FIGS. 2 and 3 are different.

Figure 3:
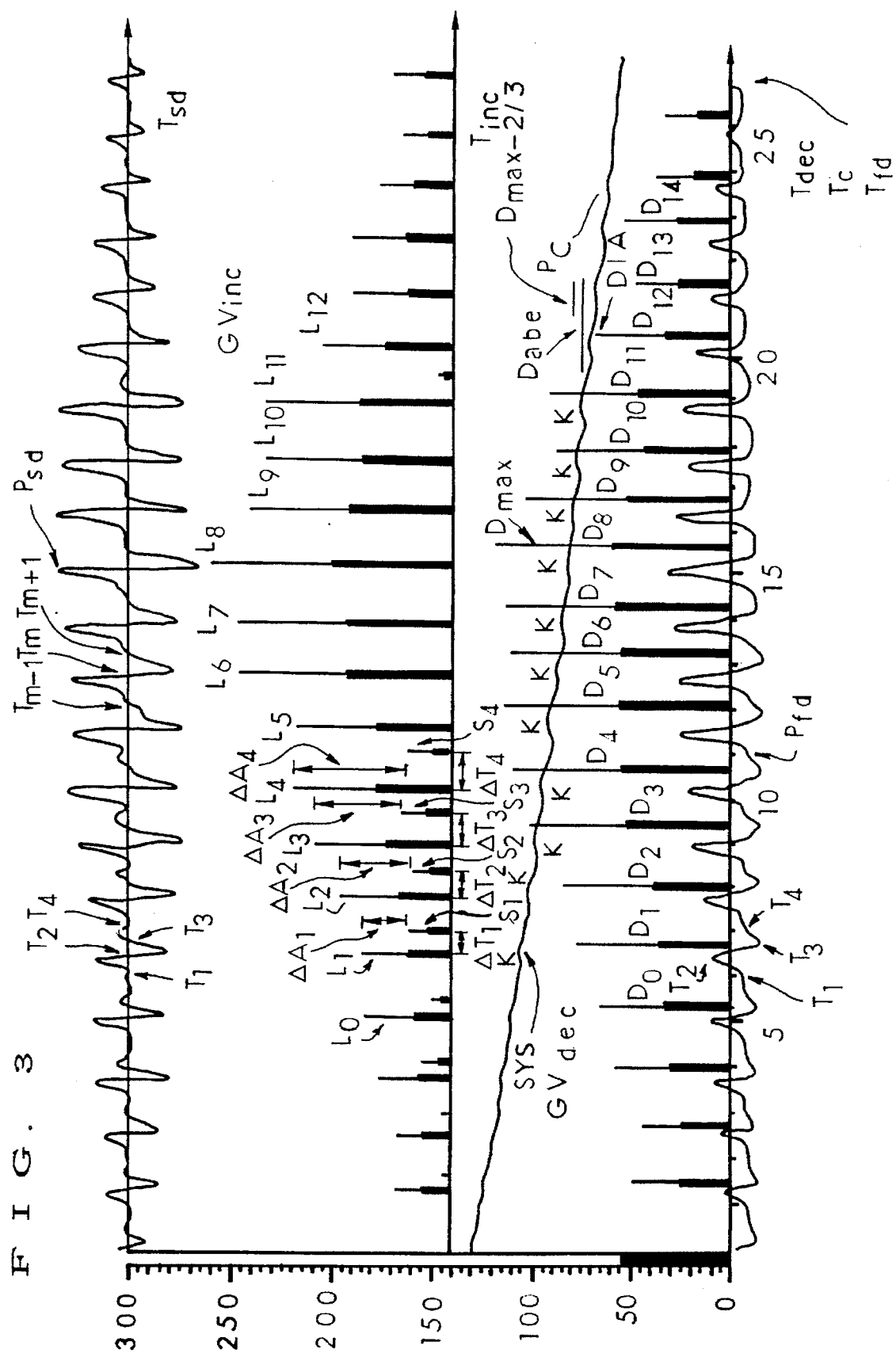
FIG. 3 is a display of the arterial response when the bleeding rate is nearly a specified constant.

Next, as shown in FIG. 3, the region surrounded by $P_{sd}$ and time axis $T_{sd}$ is subdivided by the every intersection of $P_{sd}$ and $T_{sd}$, namely T1, T2 . . . , Tm−1, Tm, Tm+1 and so on. Among them the integral over the positive region, i.e., its area, is taken as the increased value of the wall's displacement velocity Gvinc, and the area of its negative region is taken as the decreased value of the displacement velocity GVdec. Their magnitudes are respectively denoted by the length on the bar graph, namely L0, L1, and D0, D1, and so on. Their scale is enlarged on the Y-axis. Tinc and Tdec are the time scales for GVinc and GVdec, respectively, and their unit is seconds.

The means accelerating force of the expansion acting on the artery wall, GAinc, is calculated at the data processing unit 6 by dividing GVinc by the time interval for expanding the wall. The mean contracting force GAdec is calculated at unit 6 by dividing GVdec by the time interval for contracting the wall. Their magnitudes and time scales can be shown in real time on the Y- and the X-axis at the display unit 7 in a monitor similar to showing GVinc and GVdec.

According to the process for acquiring the arterial response described in this first example, the pressure fluctuation of the pulsating blood flow is effectively obtained and shown in FIGS. 2 and 3 as $P_{sd}$ along with its time trend, which is proportional to the instantaneous acceleration stretching the arterial wall.

From the instantaneous acceleration on the arterial wall motion, the change of the displacement velocity induced by the wall's stretching is calculated as the integration over the positive region of instantaneous acceleration $P_{sd}$ with respect to time. Its magnitude is shown in GVinc in FIGS. 2 and 3. The quantity corresponding to the velocity change due to the wall contraction is calculated as the integration over the negative region of instantaneous acceleration $P_{sd}$ with respect to time. Its magnitude is shown as GVdec in FIGS. 2 and 3. The quantity proportional to the average displacement acceleration acting on the wall motion is taken as GAinc and GAdec and is calculated by dividing GVinc and GVdec by the corresponding time interval for the integrations, respectively. Thus, these methods effectively acquire the noninvasive arterial response process.

Next, a second example of acquiring the arterial response using the apparatus shown in FIG. 1 is described. This method is to obtain the increments of the wall's displacement velocity at the data processing unit in the following way. The displacement velocity of the wall, $P_{fd}$, taken as the first derivative of Pc with respect to time is shown in the lower section of FIG. 3 along with acceleration $P_{sd}$ taken as the second order time derivative of Pc. The time scale of either this $P_{fd}$ or other $P_{fde}$ obtained by other methods and $T_{sd}$, namely T1, . . . Tm, and so on, the corresponding velocity components, i.e., $P_{fd}$(T1), . . . , and $P_{fd}$(Tm), are obtained. The increased or the decreased amount on the displacement velocity of the arterial wall motion, i.e., GVinc and GVdec, are obtained by the difference between the two of these. For example, L1 and D1 are proportional to $P_{fd}$(T2)–$P_{fd}$(T1) and $P_{fd}$(T3)–$P_{fd}$(T2), respectively. Furthermore, S1 is proportional to $P_{fd}$(T4)–$P_{fd}$(T3). Thus, GVinc and GVdec are divided by the corresponding time intervals and they are matched with the mean expanding and contracting accelerations GAinc and GAdec, respectively.

According to the acquired arterial response process in this second example, the pressure fluctuation of the pulsating blood flow is proportional to the instantaneous displacement velocity of the arterial wall, which is shown as $P_{fd}$ in FIGS. 2 and 3 along with its time trend. With this instantaneous velocity change on the arterial wall motion, the same GVinc and GVdec as in the first example are calculated as the changes of the displacement velocity for each stretching process. Furthermore, the mean displacement acceleration of the wall motion, as in the first example, is GAinc and GAdec, which are calculated by dividing GVinc and GVdec by each time interval, respectively. Thus, this method effectively acquires the noninvasive arterial response process.

A third example is to be explained. This uses the arterial response acquired by the above method in order to obtain a blood pressure measurement which gives nearly the same systolic and diastolic pressure readings as the auscultatory method. In this noninvasive blood pressure measurement, the following data analysis is made at unit 6. As shown in FIG. 3, when the amplitude of GVdec becomes consecutively larger than threshold Dmax-⅔ (being two-thirds of the maximum amplitude Dmax), the cuff pressure giving the closest amplitude to that threshold is taken as the pressure reading of the wave crest in the pulsating blood flow, namely systolic pressure SYS. Similarly, when the amplitude of GVdec becomes consecutively smaller than the threshold, the cuff pressure giving its first smaller amplitude is taken as the pressure reading of the wave trough in the pulsating blood flow, namely, diastolic pressure reading DIA.

According to this noninvasive blood pressure measurement method as shown in FIGS. 2 and 3, if threshold Dmax-⅔ is obtained as being two-thirds of the maximum amplitude Dmax, there are seen the GVdec's amplitudes, D1, D2, D3, etc., getting consecutively larger than the threshold. Then the cuff's pressure reading at the time when the amplitude becomes the closest to that threshold is 120 mmHg and 101 mmHg for the cases in FIGS. 2 and 3, respectively. They are the wave crest values of the pulsating blood flow, namely, the systolic pressure readings. When D7 and D8 are detected at which GVdec consecutively gets smaller than Dmax-⅔, the cuff pressure 65 mmHg which gave amplitude D7 the first smaller amplitude is the wave trough of the pulsating blood flow, namely the diastolic pressure reading. Similarly, when D12, D13 and D14 are detected at which GVdec consecutively gets smaller than Dmax-⅔, the cuff pressure 67 mmHg which gave amplitude D12 the first smaller amplitude is the wave trough of the pulsating blood flow, namely, the diastolic pressure reading.

This measuring method shows that every Korotkoff's sound simultaneously taken with a stethoscope during the measurement (labeled as k on the Pc curves in FIGS. 2 and 3), including the sound of phase 1 defining the systolic pressure reading, agrees with the pulsating process characterized with L1 and D1 in FIGS. 2 and 3. The method also shows that the annihilation of the Korotkoff's sound of phase 5 similarly agrees with the arterial wall expansion process characterized with L7 and D7 in FIG. 2, and with L12 and D12 in FIG. 3. Thus, this method is also effective as well.

Next, a fourth example is to be explained. This example is for the blood pressure measurement method giving the accurate systolic and diastolic readings by using the unique characteristics on the arterial response acquired through the method described in examples 2 and 3. The data analysis is also made at unit 6 in the following way. As shown in FIGS. 2 and 3, the unique wave form in the neighborhood of the wall's displacement acceleration $P_{sd}$ on the artery wall motion to determine the systolic pressure reading is transformed into either the changes of the time difference ΔTm between Lm and Sm in the increased displacement velocity component GVinc on the wall or their amplitudes' change ΔAm where m=1,2,3, and so on. The cuff pressure is taken as the systolic reading SYS at the time the uniqueness is found for which either of the ΔTm and the ΔAm or the both start to increase consecutively as shown in FIGS. 2 and 3. Furthermore, the mean value of the amplitudes D1 (at SYS), D0 (at right before SYS) and D2 (at right after SYS) which is indicated as Dave in FIG. 3 is obtained. The cuff pressure at the time the decreased displacement velocity component GVdec on the wall becomes consecutively smaller than either D1 or Dave is defined as the diastolic pressure reading DIA.

According to the measuring method, the unique patterns in the neighborhood of $P_{sd}$ giving the systolic pressure are obtained, as shown in FIGS. 2 and 3. They are the continuous increase as in ΔT1, ΔT2, ΔT3 and ΔT4 which are the time difference between the pairs L1 and S1, L2 and S2, L3 and S3, and L4 and S4 on GVinc; and the continuous increase of amplitude L as in ΔA1, ΔA2, ΔA3 and ΔA4. Therefore, the arterial wall stretching giving the systolic pressure shows agreement with the pulsating process characterized with L1 and D1. The systolic pressure readings are then 120 mmHg and 101 mmHg for FIGS. 2 and 3, respectively. They agree with those in the auscultatory method stated above.

Furthermore, the arithmetic average of amplitudes D1, D0 (right before) and D2 (right after) is calculated as Dave. During the course on which D12, D13 and D14 are consecutively getting smaller than either of the D1 and Dave, the cuff's pressure which gives amplitude D12 the first smaller amplitude is the diastolic pressure reading 69 mmHg which is the same as that given by the auscultatory method. As for FIG. 2, since Dave is nearly the same as Dmax-⅔, the cuff's pressure which gives amplitude D7 the first amplitude becoming smaller consecutively than either the D1 or Dave, is the diastolic pressure reading 65 mmHg. Since it is also the same as in the auscultatory method, this method is also effective for the noninvasive blood pressure measurement.

A fifth example is to be explained. This example is the blood pressure measuring method with the apparatus laid out in FIG. 1. The method is based on the acquired arterial response process being displayed in real time on the display unit 7. Following the noninvasive apparatus as shown in FIG. 1, cuff 1 being wrapped around a finger or an arm or a leg is to be inflated with a pressurizing unit 3 comprising a small pump or the like, in order to press artery 4. The cuff pressure is then detected with transducer 5 and, its pressure readings are displayed on the display unit 7 through the data processing unit 6. On a display unit 7, the pressure reading which was converted to a height information of mercury manometer at unit 6 is displayed in real time as if it were the mercury column of sphygmomanometers as shown in FIG. 4.

While watching in real time the pressure reading (the height) displayed on the mercury manometer, the cuff pressure on the subject's artery is raised a little above subject's systolic pressure reading. When the cuff's pressure starts bleeding, the time and pressure scales are displayed along the X and Y axes, respectively. Setting the time axis at arbitrary position, there are simultaneously displayed on unit 7 in real time the trend of the cuff's pressure Pc, the acceleration of the arterial wall's displacement $P_{sd}$, and the increased and decreased amount of the velocity component, GVinc and GVdec as those in the first example, or the time trend of GAinc, GAdec and $P_{fd}$.

Then, there are also displayed Dmax as shown in FIGS. 2 and 3, threshold Dmax-⅔ in FIG. 2 being calculated with Dmax, and either of D1 and Dave in the fourth example as shown in FIG. 3. Thus, it becomes possible to measure the blood pressure noninvasively while monitoring the artery response to the pulsating blood flow in real time. Further, it can store the response process at the memory unit 9. It also can transmit the acquired data from the data communication unit 10 to other instruments capable of simultaneously measuring or inversely receiving the data from them through a communication network, a telemeter and the likes.

Figure 6:
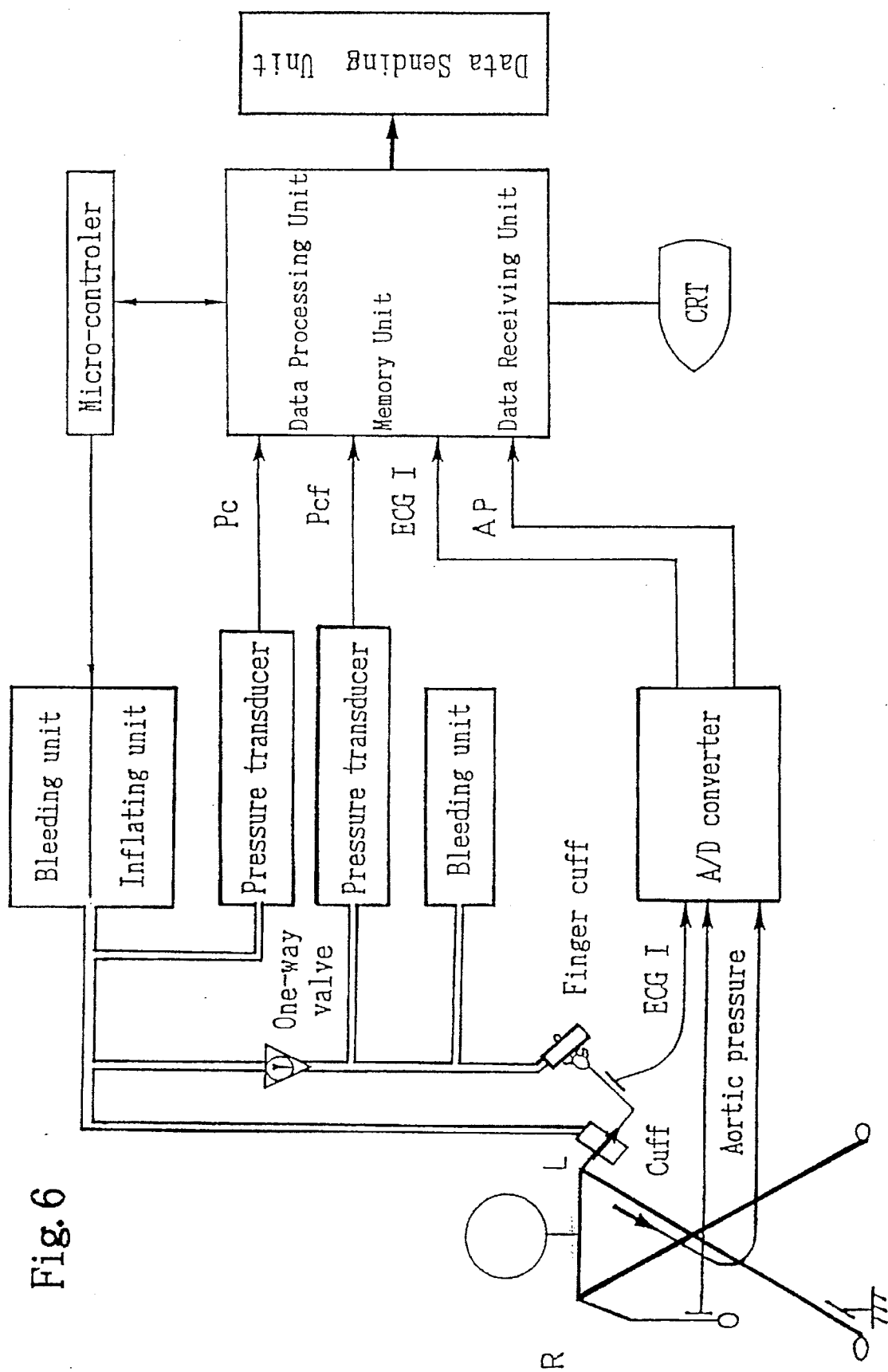
FIG. 6 is a block diagram of a second embodiment of an apparatus according to the invention.

FIG. 6 shows a second embodiment of a blood pressure measuring apparatus according to the invention. The apparatus shown therein receives other physiological signals like aortic pressure AP and ECG from other instruments through the data receiving unit. To obtain non-local information on the arterial blood circulation, the second occlusive cuff is used on finger artery down from the brachial artery. The one-way valve makes the simultaneous blood pressure measurement possible.

Figure 7:
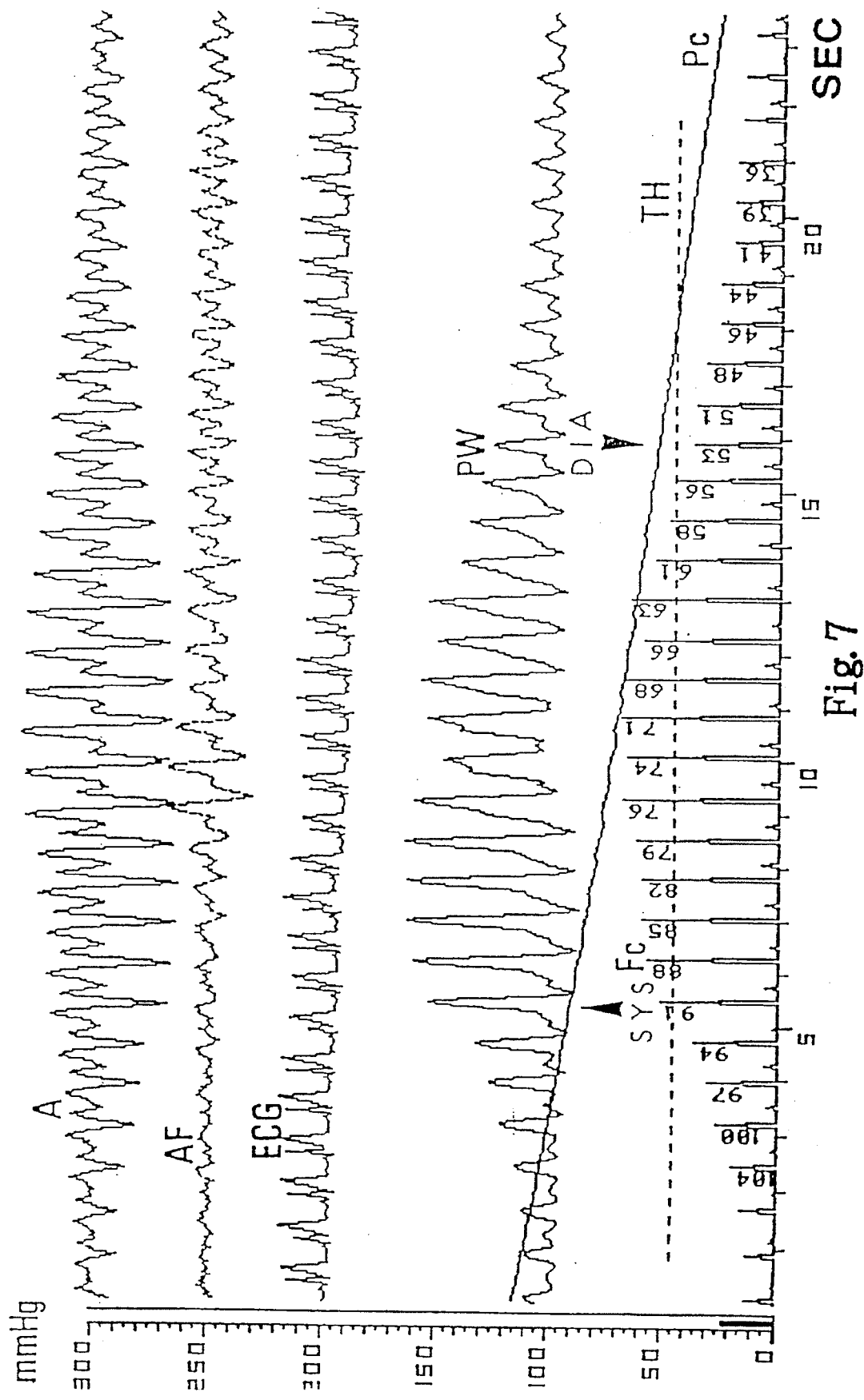
FIG. 7 is a display of the non-local arterial blood circulation where the parameter AF is the acceleration taken with a finger cuff.

FIG. 7 shows the non-local arterial blood circulation where AF is the acceleration taken with a finger cuff. Its relative magnitude is shown with the reference at 250 mmHg. The brachial SYS and DIA are indicated with arrows. This simultaneous monitoring of the brachial and finger arterial wall motions was made to study a blood pressure lowering effect due to physical exercises. A short-term lowering effect after exercises was seen among about 70 subjects who did aerobic or jogging exercises as reported by F. Takeda et al., at the 7th International Conference On Biomedical Engg., National Univ. of Singapore, December 1992, which is incorporated herein by reference.

FIG. 8-a shows a cardiac mechanical cycle which is normally triggered by the electrical cycle. Thus, the peaks of AP should be synchronized with those preceding QRS peaks. Even though some premature ventricular contractions labeled as PV are observed, it shows a nearly regular interval between every QRS and its subsequent downward peak of A that corresponds to the incisura of the AP during the course of partial occlusion by the Pc as reported by F. Takeda et al., at the 7th International Conference On Biomedical Engg., National Univ. of Singapore, December 1992, which is hereby incorporated by reference.

As for noninvasively detecting the SYS and DIA, the amplitude of AP varies significantly from one AP wave to another as seen in FIG. 8-a. So it may be impractical to determine such SYS and DIA of intra-arterial pressure waves with occlusive cuff. Yet they could be obtained reasonably well by this invention. The number labeled on Fc is the cuff's pressure reading at the time of compression. The first Fc exceeding TH has detected SYS with some inherent error while the last relatively weak two Fc's have detected each trough of the two AP waves either of which can be taken as DIA. The magnitudes of A and PW are relative with respect to their references at 300 and 100 mmHg.

In FIG. 8-b there are distinctively seen only the QRS peaks on ECG I signal. If the QRS triggers its ventricular systole, the incisura (a downward peak in A) or the Fc will never precede its triggering QRS in normal condition. However, the time interval between every pair of the QRS peak and the incisura of the Fc starts to become irregular while getting out of phase and then back in phase again depending on how long the duration between the QRS peaks is. The SYS and DIA detected in analogous to auscultation are indicated with arrows.

FIG. 8-c shows how the side pulses accompanying the main Fc's correspond with systolic murmur created with the aortic valve. Thus, some deformity in the aortic valve appears to have created another small pulsation on its main arterial pressure pulse, which could not be detected by ECG.

FIG. 8-d shows how an atrial fibrillation which appears too rapid for ventricular systoles to be triggered causes an irregular heart rate.

The figures from 9-a to 8-j show velocity and acceleration detection functions and power detection.

Velocity detection function

Taking a correlation integral of cuff pressure Pc(t) and a velocity detection function $\phi$ v(t-m) with respect to time t as shown in FIG. 9-a, one finds V aside from a proportional constant:

$$V = \int dt\, Pc\,(t)\, \phi v(t-m) = 4\tau\{\overline{Pc(m)} - \overline{Pc(m-4\tau)}\} \quad 1)$$

where the integration limit is from $-\infty$ to $+\infty$, although the effective integration limit is (m−8τ, m]. The open and closed interval is indicated with (and ], respectively. The m which is a positive integer is a present time and τ is a time interval. $\overline{Pc(m)}$ and $\overline{Pc(m-4\tau)}$ are the time averages of Pc(t) over time intervals (m−4τ, m] and (m−8τ, m], respectively. These intervals can be set at any time separation. If Pc(t) is sampled at every time interval τ, its discrete time signal of Pc(t) will be given, for instance, as Pm at time m. Using this Pm, Eq. (1) is:

$$= \tau \quad \{(Pm - Pm - 4\tau) + (Pm - 1\tau - Pm - 5\tau) + \quad (2)$$
$$(Pm - 2\tau) - Pm - 6\tau) + (Pm - 3\tau - Pm - 7\tau)\}$$
$$= 4\tau \quad \{(<Pm>_4 - <Pm - 1\tau>_4) +$$
$$(<Pm - 1\tau>_4 - <Pm - 2\tau>_4) +$$
$$(<Pm - 2\tau>_4 - <Pm - 3\tau>_4) +$$
$$(<Pm - 3\tau>_4 - <Pm - 4\tau>_4)\}$$
$$= 16\tau \quad \{<\Delta<Pm>_4>_4\}$$

where $\Delta$ is the first order difference and $<>$ is a moving average defined as:

$$<Pm>_4 = 1/4 \sum_{k=0}^{3} Pm - k \cdot \tau$$

If another velocity detection function $\phi$ v(t−m) shown in FIG. 9-b is used, the last moving average in Eq. (2) can be taken out:

$$V = \int dt\, Pc(t)\, \phi v(t-m) = 4\tau \{\Delta<Pm>_4\} \quad (3)$$

Acceleration detection function

Taking a correlation integral of cuff pressure Pc(t) and an acceleration detection function $\phi$ a(t−m) with respect to time t as shown in FIG. 9-c, one finds aside from a proportional constant:

$$A = \int dt\, Pc(t)\, \phi a(t-m) = 16 \cdot \tau \cdot 4 \{<\Delta<\Delta<Pm>_4>_4>_4\} \quad (4)$$

where the integration will be carried from $-\infty$ to $+\infty$, although the effective integration limit is (m−12τ, m].

If another acceleration detection function $\phi$ a(t−m) shown in FIG. 9-d is used, the last moving average in Eq. (4) can be taken out;

$$A = \int dt\, Pc(t)\, \phi a(t-m) \quad (5)$$
$$= 16 \cdot \tau \{\Delta<\Delta<Pm>_4>_4\}$$

As for the functional form, there are many modifications like those shown in FIGS. 9-e and 9-f. Although the square waves are used for velocity and acceleration detecting functions, any functional shape could be used as long as the first order difference can be made; namely, as long as there exist a pair of plus and negative regions in the function.

Power detecting functions

Aside from a proportional constant, power PW can be defined as the product of velocity V and acceleration A detected with their own detecting functions shown in FIGS. 9g and 9-h. If a pair of velocity and acceleration detecting functions are orthogonal to each other like those shown in FIGS. 9-i and 9-j, the coefficient of their tensor product can be any pair product of velocity V and acceleration A detected with Eqs. (2) and (3), and Eqs. (4) and (5), respectively. The product is proportional to its power. From these power PW, their energy Es and Ec can be calculated as the integral of positive and negative PW, respectively.

FIG. 10-a shows a time history of PW taken with a power detection function shown in FIG. 9-g as the cuff occluding brachial artery was inflated with a DC driven mechanical pump. Its magnitude is relative with respect to the reference at 0 mmHg and time in sec is on the X-axis. Velocity V and acceleration A are taken with their own detecting function shown in FIGS. 9b and 9-d. Their relative magnitudes are also shown with respect to the references; 330 mmHg and 230 mmHg, respectively. They show noisy pressure fluctuations in the cuff pressure which were created with the mechanical vibration of pump.

A time history of Energy Ec whose magnitude is relative with respect to the reference at −50 mmHg is shown just below PW. The amplitude of Ec which is proportional to the integration of negative PW will become large enough to be detected only when the partial constraint is effective. The partial constraint starts when Pc approaches one of the AP's troughs and ends when Pc goes above one of the AP's crests. Thus, the Pc's reading at the PW's peak right before the last effective Ec gives SYS during the noisy auto-inflation process. A time history of ECG I is also shown with respect to the reference at 150 mmHg and its magnitude is relative.

FIG. 10-b shows a continuation of the measurement started as in FIG. 10-a. It has changed into a quiet and constant deflation process. As seen, the partial constraint, which now starts when Pc gets to one of the AP's crests and ends when Pc approaches one of the AP's troughs, reflects the large amplitude changes in PW and Ec. A threshold level for Ec and PW can be easily set for detecting DIA as their maximum amplitudes before the beginning of the partial constraint which gives SYS. Thus, the first amplitude in Ec or PW comparable with or less than the threshold gives DIA. The maximum amplitudes are indicated with arrows.

FIG. 10-c shows the same data as FIG. 10-b except for PW which is now taken with a different pair of detecting functions shown in FIG. 9-j to magnify the negative region of PW.

FIG. 10-d is taken from the same subject as in FIG. 8-a where it was difficult to determine SYS and DIA even in a quiet and constant deflation process. For such a subject, Ec clearly detected DIA and SYS during the noisy auto-inflation process.

Therefore, according to this noninvasive measurement, the arterial response characterized by the wall motion can be monitored in real time. Thus, transmitting the monitored data to other instruments becomes possible. Reversibly, it becomes possible first to receive the data from the other instruments capable of simultaneously monitoring the same object, for example, a ECG monitor and the likes, and then to display it as an analog quantity in real time. As this result, the noninvasive blood pressure measurement can be effectively made.

In summary, a method of measuring blood pressure comprises inflating a cuff, determining changes in power, and determining changes in energy of the arterial wall motion as the wall stretches and contracts in response to a pulsating blood flow through the artery. Additionally, the method includes comparing the changes in power or energy to determine diastolic and systolic pressure readings as indicated by the cuff pressure, comparing the changes in power or energy to detect systolic pressure and to stop inflation, and starting deflation of the cuff pressure to measure blood pressure.

More particularly, the method includes determining instantaneous velocity and acceleration of the arterial wall displacement (motion) by acquiring the instantaneous velocity of the arterial wall's displacement with velocity and acceleration detection functions. Additionally, the method includes acquiring the instantaneous power of the arterial wall's displacement with power detection functions. The method further includes taking the positive area (portion) of the power to determine the stretching energy of the wall motion, and taking the negative area (portion) of the power to determine the compressing energy of the wall motion.

The step of comparing changes in the compressing energy to determine diastolic and systolic pressure readings during inflating (increasing) cuff pressure includes detecting the first effective amplitude in the compressing energy, and detecting a maximum amplitude of power at right before the detected first effective amplitude to determine diastolic pressure. A threshold of power amplitude is established, and the method includes detecting a consecutive decreased power amplitude that is less than the threshold level to determine systolic pressure. Alternatively, the method includes detecting the last effective amplitude in the compressing energy to determine systolic pressure at a maximum amplitude in power right before the last effective amplitude, and stopping inflating cuff pressure and starting deflating (decreasing) cuff pressure to detect systolic and diastolic pressure again in a continuous manner.

In another aspect of the method, the step of comparing changes in power to determine diastolic and systolic pressure readings during deflating cuff pressure includes detecting a sudden increase in the amplitudes in power to determine systolic pressure, detecting a maximum amplitude of power at right before that first sudden increase, establishing a threshold or power amplitude, and detecting a consecutive decreased power amplitude that is less than the threshold level to determine diastolic pressure. Alternatively, diastolic pressure may be determined by detecting a sudden decrease in the amplitudes in power.

The step of comparing the changes in the compressing energy to determine systolic and diastolic pressure readings during deflating cuff pressure may comprise detecting the first sudden increase in amplitudes in the compressing energy, and detecting a maximum amplitude of power occurring before the first effective amplitude to determine systolic pressure. Further included in this step is establishing a threshold of power amplitude and detecting a consecutive decreased power amplitude that is less than the threshold level to determine diastolic pressure. Alternatively, systolic pressure may be determined by detecting the last effective amplitude in the compressing energy at a maximum amplitude in power immediately before its last effective amplitude. The method may further include a maximum amplitude of compressing energy at right before that first effective amplitude of compressing energy, establishing a threshold of compressing energy amplitude, and detecting a consecutive decreased amplitude of compressing energy that is less than the threshold level to determine diastolic pressure.

The step of comparing the changes in energy to determine systolic and diastolic pressure readings during deflating the cuff pressure may include detecting a sudden increase in the amplitudes in stretching energy to determine systolic pressure and detecting a sudden decrease in the amplitudes in stretching energy to determine diastolic pressure.

A blood pressure measuring apparatus, according to the invention, may include a first cuff having tubes therein for wrapping around the applying pressure to an artery and a second cuff having tubes therein for wrapping around the applying pressure to another artery. Additionally, the apparatus may include a one-way valve, a first pressure transducer, a second pressure transducer, a first bleeding valve, and a second bleeding valve. With this apparatus, the blood pressure may be simultaneously determined in both arteries. The apparatus further allows for simultaneously acquiring dynamic parameters of the arterial wall motion and simultaneously displaying the dynamic parameters on a display unit.

More particularly, the blood pressure measuring apparatus includes a data receiving unit for continuously receiving or transmitting other physiological data from or to other instruments.

From another perspective, the invention is a method of measuring dynamic parameters of arterial wall motion against increasing or decreasing pressure of a pressurized cuff, including inflating the cuff pressure to increase the cuff pressure, determining power of the arterial wall's displacement as the wall stretches and contracts, and from the power, determining changes in energy of the arterial wall motion over time.

The method may further include determining the instantaneous velocity and acceleration of the arterial wall's displacement and multiplying the velocity and the acceleration to determine the power. The method may further include acquiring the instantaneous velocity of the arterial wall's displacement with velocity and acceleration detection functions and acquiring the instantaneous power of the arterial wall's displacement with power detection functions. From the power, the positive area of the power may be taken to determine the stretching energy of the wall motion, and the negative area of the power may be taken to determine the compressing energy of the wall motion. The velocity, acceleration, power and energy as a function of time may then be displayed on a display unit.

Having illustrated and described the principles of the invention in a preferred embodiment, it should be apparent to those skilled in the art that the invention can be modified in arrangement and detail without departing from such principles. For example, discrete or integrated components of various types may be employed for the various parts of the apparatus, as is known to those of skill in the art. Features of the invention shown in software may also be implemented in hardware.

Therefore, the illustrated embodiments should be considered only as preferred examples of the invention and not as a limitation on the scope of the claims. I therefore claim as my invention all modifications and equivalents to the illustrated embodiments coming within the scope and spirit of following claims.

I claim:

1. A method for measuring dynamic parameters of arterial wall motion, comprising:

presurizing a cuff that surrounds an artery;

measuring the cuff pressure;

determining from the cuff pressure a velocity and acceleration of the arterial wall; determining power of the arterial wall motion as the wall stretches and contracts in response to the cuff pressure, the power being defined as the product of the velocity of the arterial wall and the acceleration of the arterial wall; and from the power, determining changes in energy of the arterial wall, the energy being defined as the power measured over a predetermined time.

2. The method of claim 1 wherein the velocity, acceleration and power are obtained with the following steps:

acquiring velocity and acceleration of the arterial wall motion with velocity and acceleration detection functions;

determining instantaneous power of the arterial wall motion from the velocity and acceleration;

determining what portion of power is positive to determine a stretching energy of the wall motion; and determining what portion of power is negative to determine a compressing energy of the wall motion.

3. An apparatus for measuring dynamic parameters of arterial wall motion, comprising:

an inflatable cuff;

a pressurizing device for inflating the cuff to increase the cuff pressure;

a pressure transducer for monitoring the pressure in the cuff and producing an electric signal related to the pressure; and a data processor communicable with the pressure transducer to receive the electrical signal, the data processor programmed for:

determining, from the cuff pressure, a velocity and acceleration of the arterial wall;

determining power of the arterial wall motion as the wall stretches and contracts in response to the cuff pressure, the power being defined as the product of the velocity of the arterial wall and the acceleration of the arterial wall; and from the power, determining changes in energy of the arterial wall, the energy being defined as the power measured over a predetermined time.

4. A method for measuring blood pressure by measuring dynamic parameters of arterial wall motion, comprising:

pressurizing a cuff that surrounds an artery;

measuring the cuff-pressure; determining from the cuff pressure a velocity and acceleration of the arterial wall;

determining power of the arterial wall motion from the product of the velocity of the arterial wall and the acceleration of the arterial wall; and determining blood pressure from the power of arterial wall motion.

5. The method of claim 4 including the step of determining, from the power, changes in energy of the arterial wall.

* * * * *